(12) United States Patent
Aharoni et al.

(10) Patent No.: US 8,940,961 B2
(45) Date of Patent: Jan. 27, 2015

(54) PLANT TRANSFORMED WITH HARDY (HRD) GENE HAVING ENHANCED DROUGHT TOLERANCE

(75) Inventors: Asaph Aharoni, Wageningen (NL); Shital Dixit, Wageningen (NL); Kurniawan Rudi Trijatmiko, Wageningen (NL); Jelle Hiemstra, Wageningen (NL); Andy Pereira, Wageningen (NL)

(73) Assignee: Stiching Dienst Landbouwkundig Onderzoek, Wageningen (NL)

( * ) Notice: Subject to any disclaimer, the term of this patent is extended or adjusted under 35 U.S.C. 154(b) by 1630 days.

(21) Appl. No.: 11/991,724

(22) PCT Filed: Sep. 6, 2005

(86) PCT No.: PCT/NL2005/000644
§ 371 (c)(1),
(2), (4) Date: Mar. 25, 2011

(87) PCT Pub. No.: WO2007/030001
PCT Pub. Date: Mar. 15, 2007

(65) Prior Publication Data
US 2011/0209247 A1    Aug. 25, 2011

(51) Int. Cl.
*C12N 15/29* (2006.01)
*C12N 15/82* (2006.01)
*C07K 14/415* (2006.01)

(52) U.S. Cl.
CPC .......... *C12N 15/8273* (2013.01); *C07K 14/415* (2013.01); *C12N 15/8261* (2013.01); *C12N 15/827* (2013.01); *C12N 15/8279* (2013.01); *C12N 15/8282* (2013.01)
USPC ......................................... 800/279; 800/287

(58) Field of Classification Search
None
See application file for complete search history.

(56) References Cited

FOREIGN PATENT DOCUMENTS

| EP | 1 457 564 | 9/2004 |
|---|---|---|
| WO | 2004/031349 | 4/2004 |
| WO | WO2004031349 A2 * | 4/2004 |

OTHER PUBLICATIONS

Hao et al. Unique mode of GCC box recognition by the DNA-binding domain of ethylene-responsive element binding factor (ERF domain) in plant. Journal of Biological Chemistry. 1998. 273(41): 26857-26861.*
Magnani et al. From endonucleases to transcription factors: evolution of the AP2 biding domain in plants. The Plant Cell. 2004. 16: 2265-2277.*
Qin et al. Isolation and characterization of an ERF-like gene from *Gossypium barbadense*. Plant Science. 2004. 167: 1383-1389.*
GenBank Accession No. ABN50365.1. Ethylene responsive element binding protein. Direct Submission. Published Feb. 19, 2007.*
Database Geneseq [Online] "Transcription factor G1753 coding sequence, SEQ ID 271." XP002377265(2004) retrieved from EBI accession No. GSN:AD061804.
Database Geneseq [Online] "Transcription factor G1753, SEQ ID 272." XP002377266(2004) retrieved from EBI accession No. GSN:AD061805 Protein sequence (Seq. ID No. 272 of WO2004031349) 100% identical to Seq ID No. 3 of the application.
Sakuma, Y., et al. "DNA-Binding Specificity of the ERF/AP2 Domain of *Arabidopsis* DREBs, Transcription Factors Involved in Dehydration- and Cold-Inducible Gene Expression" *Biochemical and Biophysical Research Communications* (2002) vol. 290, No. 3, pp. 998-1009.
Nakano, T., et al "Genome-Wide Analysis of the ERF Gene Family in *Arabidopsis* and Rice[TM]." Plant Physiology (2006) vol. 140, No. 2, pp. 411-432.
Ng, Pauline C., et al. "SIFT: predicting amino acid changes that affect protein function", Nucleic Acids Research, 2003, vol. 31, No. 13, pp. 3812-3814.
Hu, Honghong, et al., "Overexpressing a NAM, ATAF, and CUC (NAC) transcription factor enhances drought resistance and salt tolerance in rice", PNAS, Aug. 29, 2006, vol. 103, No. 35, pp. 12987-12992.
Finkelstein, Ruth R., et al., "ABA and sugar interactions regulating development: cross-talk or voices in a crowd?", Current Opinion in Plant Biology, 2001, vol. 5, pp. 26-32.
Kerepesi, Ildiko, et al., "Osmotic and Salt Stress-Induced Alteration in Soluble Carbohydrate Content in Wheat Seedlings", Crop Science, Mar.-Apr. 2000,vol. 40. pp. 482-487.
Ng, Pauline C., et al., "Predicting Deleterious Amino Acid Substitutions" Genome Research, 2001, vol. 11. pp. 863-874.
Kasuga M, et al. A combination of the *Arabidopsis* DREB1A gene and stress-inducible rd29A promoter improved drought- and low-temperature stress tolerance in tobacco by gene transfer. Plant Cell Physiol. 45, 346-350 (2004).
Hsieh TH, Lee JT, Charng YY, Chan MT (2002) Tomato plants ectopically expressing *Arabidopsis* CBF1 show enhanced resistance to water deficit stress. Plant Physiol. 130:618-626.

(Continued)

*Primary Examiner* — Cathy Kingdon Worley
*Assistant Examiner* — Ashley K Buran
(74) *Attorney, Agent, or Firm* — Ladas & Parry LLP

(57) ABSTRACT

Transgenic plants with novel phenotypes, especially plants with enhanced drought and pathogen resistance. Provided are transgenic crop plants having integrated in their genome a chimeric gene, wherein the chimeric gene includes a transcription regulatory sequence active in plant cells operably linked to a nucleic acid sequence encoding a protein having the sequence of SEQ ID NO: 3 or a protein at least 70% identical to SEQ ID NO: 3 or an ortholog or a functional fragment thereof. In addition to enhanced drought tolerance the transgenic plants may show enhanced disease resistance and enhanced root structure. Also, a method for generating a transgenic plant by insertion of the chimeric gene.

12 Claims, 7 Drawing Sheets

(56) References Cited

OTHER PUBLICATIONS

Hsieh TH, Lee JT, Yang PT, Chiu LH, Charng YY, Wang YC, Chan MT (2002). Heterology expression of the *Arabidopsis* C—repeat/dehydration response element binding factor 1 gene confers elevated tolerance to chilling and oxidative stresses in transgenic tomato. Plant Physiol. 129: 1086-1094.

Oh SJ, Song SI, Kim YS, Jang HJ, Kim SY, Kim M, Kim YK, Nahm BH, Kim JK (2005). *Arabidopsis* CBF3/DREB1A and ABF3 in transgenic rice increased tolerance to abiotic stress without stunting growth. Plant Physiol. 138: 341-351.

Gutterson N, Reuber TL, Regulation of disease resistance pathways by AP2/ERF transcription factors. Current Opinion in Plant Biology. 2004, 7:465-471.

Hou Bing-Kai, Xia Guan-Min, Chen Zheng-hua (2001) Strategies for Optimizing Expression Vectors Used in Plant Genetic Engineering HEREDITAS (Beijing) 23(5) : 492497.

\* cited by examiner

Fig. 1A    *hardy* mutant phenotype
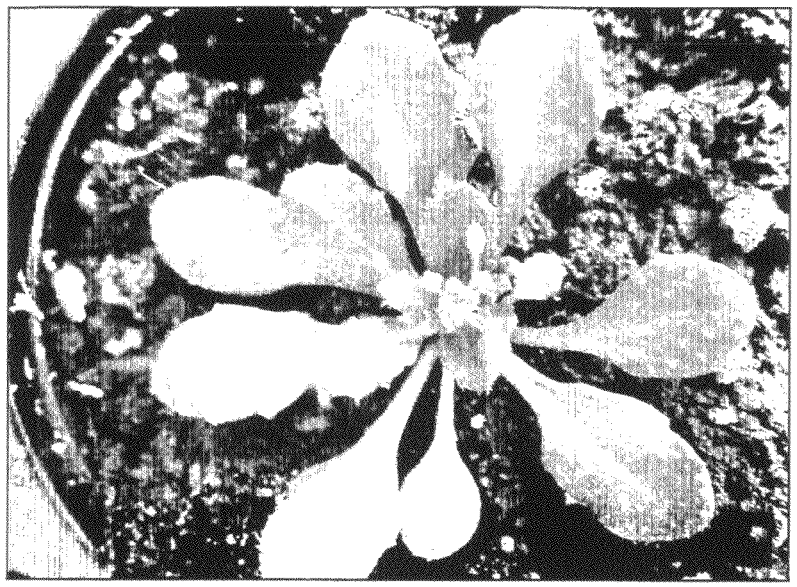
Fig. 1B
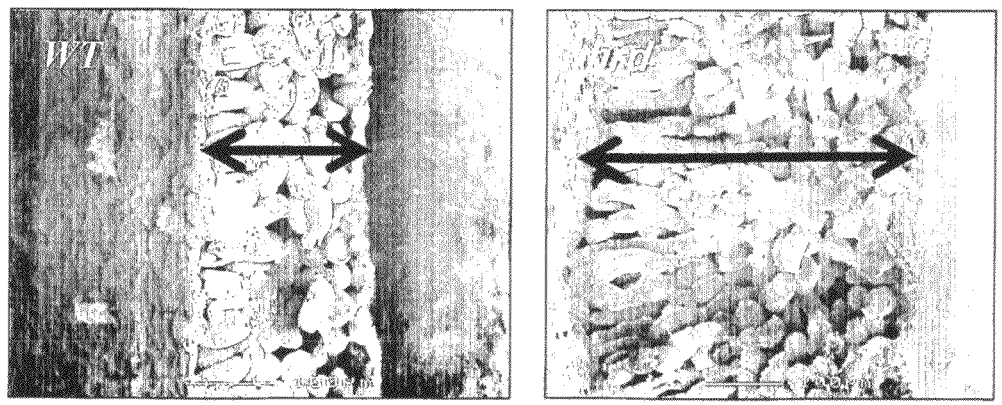

Fig. 2  Root structure of the *hrd* mutant
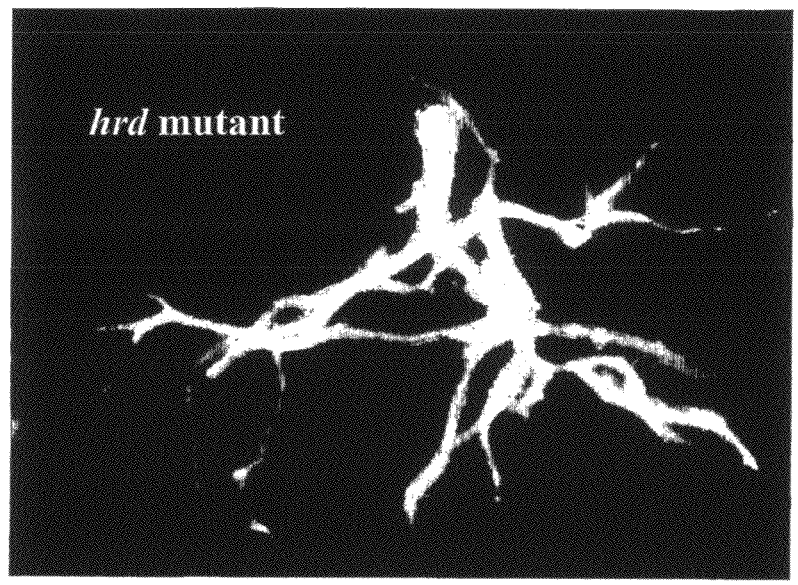
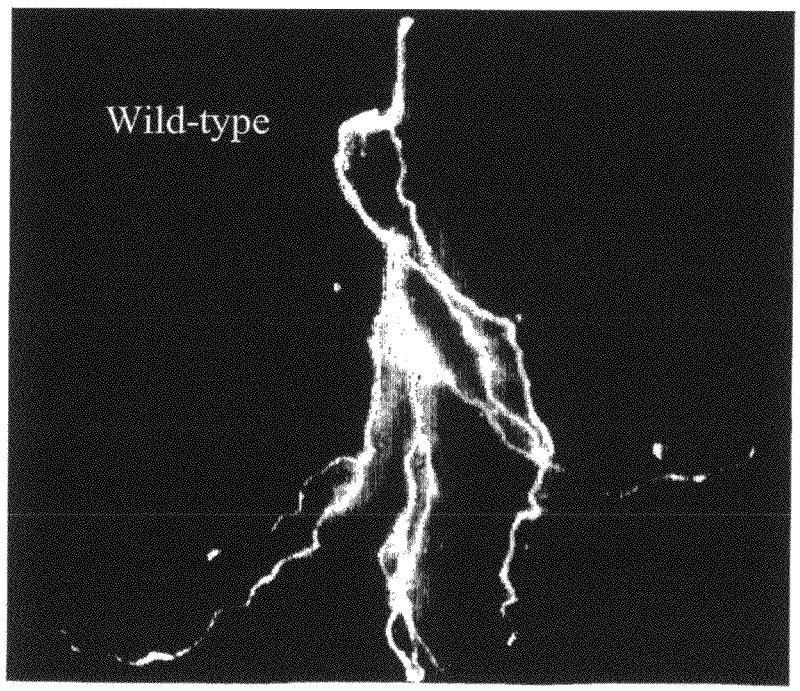

Fig. 3A    *hrd* mutant genomic structure

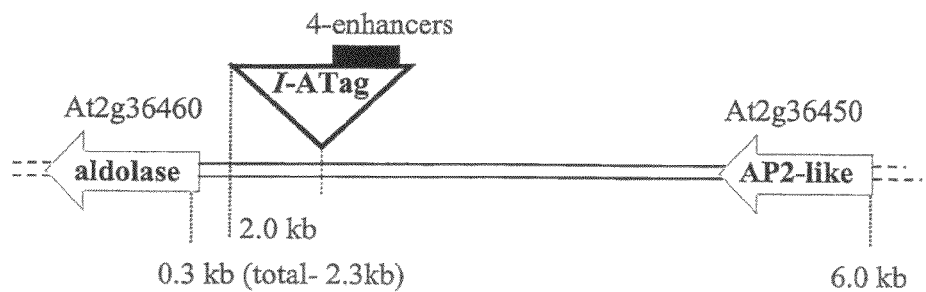

Fig. 3B    RT-PCR analysis of candidate tagged genes
in the *hrd* mutant

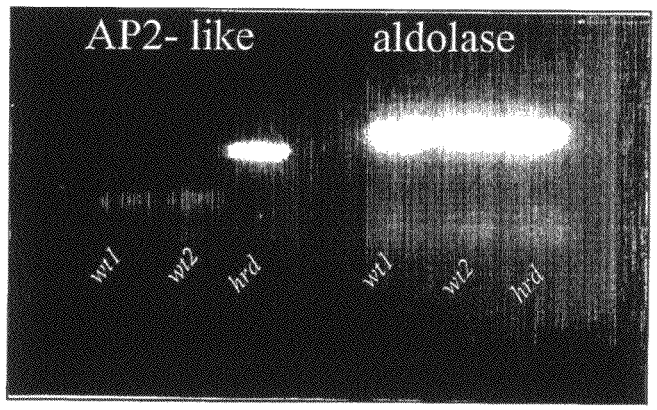

Fig. 3C    HRD Protein sequence showing AP2 domain

```
MQGTSKDNGGRHPLYRGVRQRKNSNKWVSEIREPRKPNRIWLGTFSTPEM
AAIAYDVAALALKGSQAELNFPNSVSSLPAPTSMSPADIQAAAASAAAAF
GAARDAIVMANNNSQTSGVACMNSSYDNTNMNGFMDEDLVFDMPNVLMNM
AEGMLLSPPRPTVFDAAYDADGFPGGDDYLWNFP
```

Fig 4    Induction of mutant phenotype by DEX
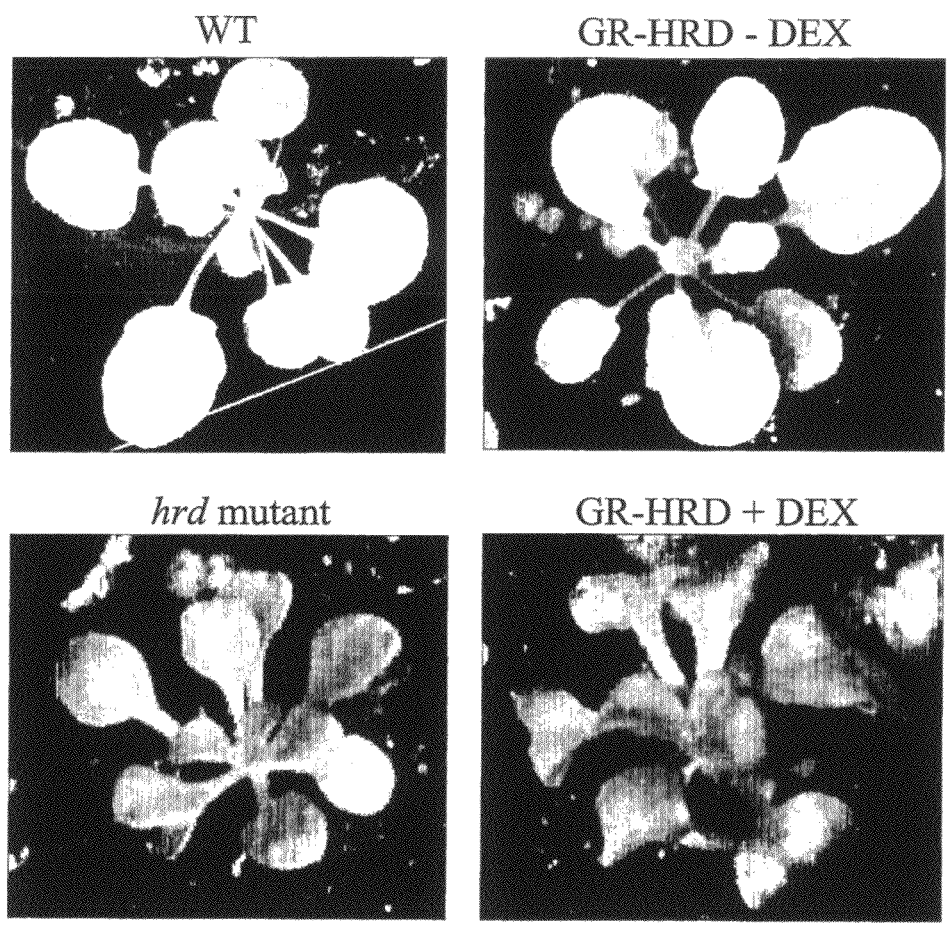

Fig 5    Drought resistance of hrd mutant
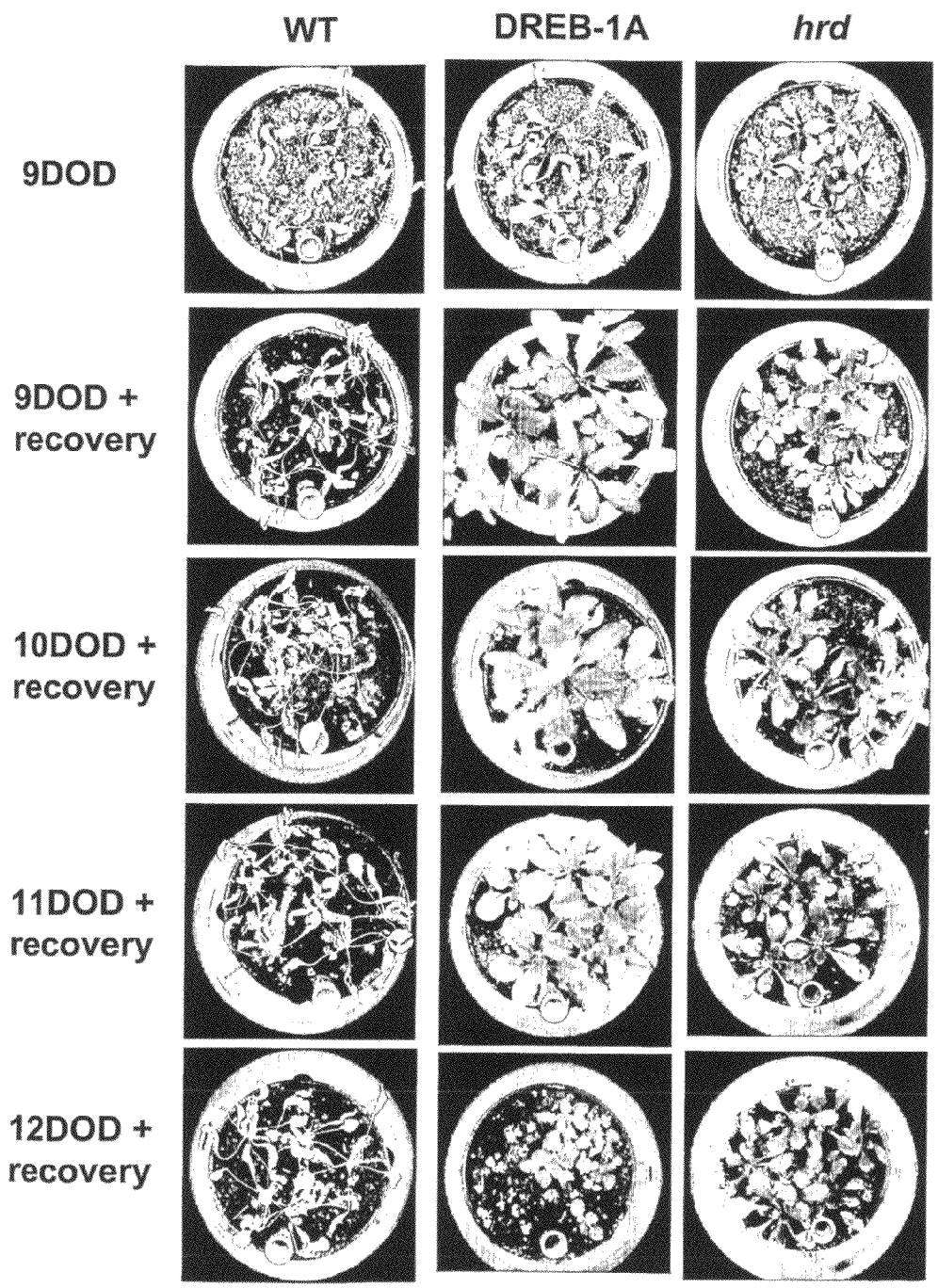

Fig 6  Drought resistance induction of HRD-GR
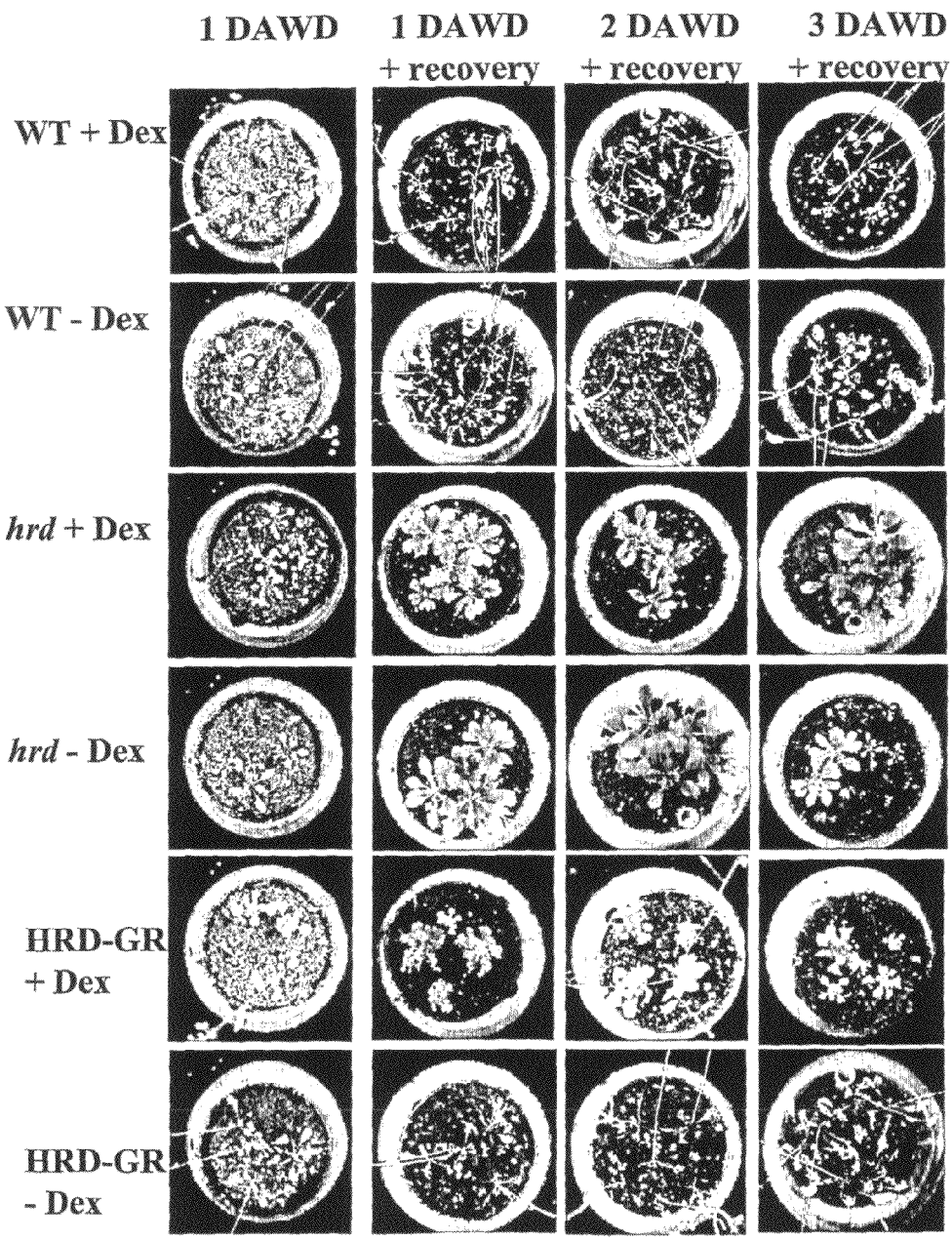

Fig 7    Pathogen resistance of *hrd* to Verticillium
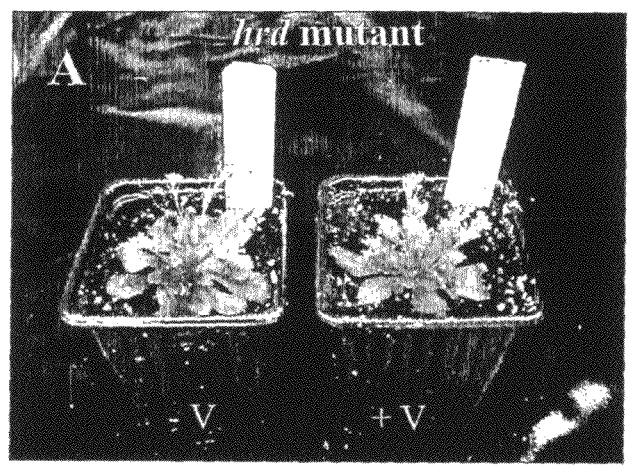
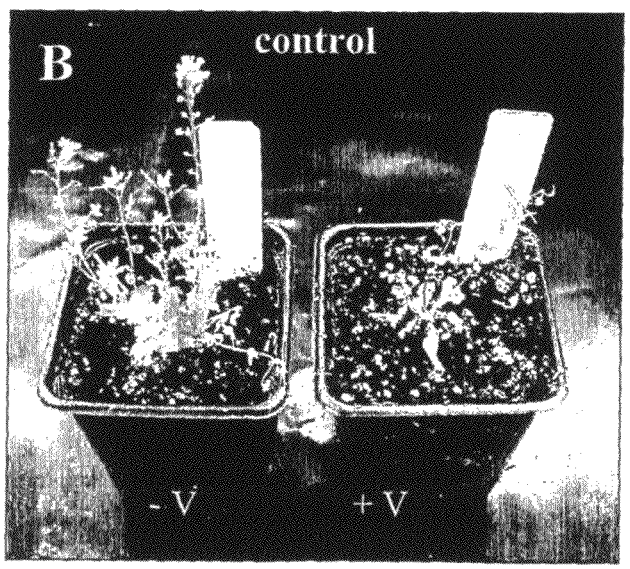

PLANT TRANSFORMED WITH HARDY (HRD) GENE HAVING ENHANCED DROUGHT TOLERANCE

FIELD OF THE INVENTION

The present invention relates to transgenic crop plants having enhanced drought tolerance. The invention further provides chimeric genes, nucleic acid vectors and methods for the generation of transgenic plants with enhanced drought tolerance.

BACKGROUND OF THE INVENTION

Plants are constantly challenged by environmental stress factors that affect their survival. Adverse biotic and abiotic stress factors can reduce the growth and productivity of plant crops. As tolerance to biotic and abiotic stresses has a direct impact on plant productivity (yield and product quality), mechanisms for conferring or enhancing stress tolerance have been widely studied and various approaches for conferring environmental stress tolerance have been described in the art. However, while most studied mechanisms are on either biotic or abiotic stress interactions, in nature plants respond and resist multiple stress factors.

Environmental stress factors have been estimated to cause depreciation in crop yield up to 70% when compared to the yield under favorable conditions (Boyer, Science 218, 443-448, 1982). Stability of crops to changes in environmental factors are therefore one of the most valued traits for breeding. However, traditional breeding is thwarted by the complexity of stress tolerance traits, low genetic variance of yield components and the lack of efficient selection techniques. It might therefore be useful to follow specific genes coding for stress tolerance components, in breeding by marker-assisted selection as well as by genetically engineering plants to be more stress tolerant.

Amidst the complexities of environmental stress reactions in crop plants the use of the simple model *Arabidopsis*, offers an opportunity for the precise genetic analysis of stress reaction pathways common to most plants. The relevance of the *Arabidopsis* model is evident in recent examples of improving drought, salt and freezing tolerance (Jaglo-Ottosen et al., Science 280, 104-106, 1998; Kasuga et al., Nat. Biotechnol. 17, 287-291, 1999) using genes identified in *Arabidopsis*. These genes are transcription factors of the ERF/AP2 family that regulate the expression of a number of downstream genes conferring stress resistance in a number of heterologous plants.

One of the most serious abiotic stresses plants have to cope with world-wide is drought stress or dehydration stress. Four-tenths of the world's agricultural land lies in arid or semi-arid regions. Apart from that, also plants grown in regions with relatively high precipitation may suffer spells of drought throughout the growing season. Many agricultural regions, especially in developing countries, have consistently low rain-fall and rely on irrigation to maintain yields. Water is scarce in many regions and its value will undoubtedly increase with global warming, resulting in an even greater need for drought tolerant crop plants, which maintain yield levels (or even have higher yields) and yield quality under low water availability. It has been estimated that the production of 1 kg of cotton requires about 15,000 liters of water in irrigated agriculture, while 1 kg of rice requires 4000 liters. Enhancing or engineering the tolerance of crop plants to short and long spells of drought and reducing the water requirement of crops grown in irrigated agriculture is clearly an important objective.

Although breeding (e.g. marker assisted) for drought tolerance is possible and is being pursued for a range of crop species (mainly cereals, such as maize, upland rice, wheat, sorghum, pearl millet, but also in other species such as cowpea, pigeon pea and *Phaseolus* bean), it is extremely difficult and tedious because drought tolerance or resistance is a complex trait, determined by the interaction of many loci and gene-environment interactions. Single, dominant genes, which confer or improve drought tolerance and which can be easily transferred into high yielding crop varieties and breeding lines are therefore sought after. Most water is lost through the leaves, by transpiration, and many transgenic approaches have focused on modifying the water loss through changing the leaves. For example WO00/73475 describes the expression of a C4 NADP+-malic enzyme from maize in tobacco epidermal cells and guard cells, which, according to the disclosure, increases water use efficiency of the plant by modulating stomatal aperture. Other approaches involve, for example, the expression of osmo-protectants, such as sugars (e.g. trehalose biosynthetic enzymes) in plants in order to increase water-stress tolerance, see e.g. WO99/46370. Yet other approaches have focused on changing the root architecture of plants.

To date another promising approach to enhance drought tolerance is the overexpression of CBF/DREB genes (DREB refers to dehydration response element binding; DRE binding), encoding various AP2/ERF (ethylene response factor) transcription factors (WO98/09521). Overexpression of the CBF/DREB1 proteins in *Arabidopsis* resulted in an increase in freezing tolerance (also referred to as freeze-induced dehydration tolerance) (Jaglo-Ottosen et al., Science 280, 104-106, 1998; Liu et al., Plant Cell 10, 1391-1406, 1998; Kasuga et al., Nat. Biotechnol. 17, 287-291, 1999; Gilmour et al. Plant Physiol. 124, 1854-1865, 2000) and enhanced the tolerance of the recombinant plants to dehydration caused either by water deficiency or exposure to high salinity (Liu et al., 1998, supra; Kasuga et al., 1999, supra). Another CBF transcription factor, CBF4, has been described to be a regulator of drought adaptation in *Arabidopsis* (Haake et al. 2002, Plant Physiology 130, 639-648).

Despite the availability of some genes which have been shown to enhance drought tolerance in a number of plant species, such as Brassicaceae and Solanaceae, there is a need for the identification of other genes with the ability to confer or improve drought tolerance when expressed in crop plants. In one embodiment, the present invention provides a new gene and associated mechanism which fulfil this need.

Biotic stresses like pathogen (bacteria, fungi, virus) or pests (insect, nematode) are the most common and a number of mechanisms normally protect plants against most of these threats. However, in certain cases plants display a susceptible reaction to specific pathogens or pests and are considered as host for the particular pathogen or pest. The host-pathogen interaction has been well characterized by the gene-for-gene concept where specific genes from the host plant and a pathogen/pest interact to either display a susceptible or a resistant reaction. Though the molecular genetics of such interactions have been well characterized in recent years, the use of such simple resistance genes has been hampered by the versatile mutability of the pathogen system that produces the diversity to overcome the resistance genes. In general the resistance genes belong to a few general classes of proteins that comprise of leucine rich repeats and additional domains. Though these genes and genetic interactions are interesting to study plant pathogen interactions, their employment for crop protection against a wider diversity and range of pathogens is still a ways away. Another way that can provide resistance is to use genes that are involved in the protection of plants to a diverse range of pathogens using mechanisms that do not rely on recognition of plant and pathogens. This would confer a non race specific resistance which is broader as it would confer resistance to a wider range of pathogens.

GENERAL DEFINITIONS

The term "nucleic acid sequence" (or nucleic acid molecule) refers to a DNA or RNA molecule in single or double stranded form, particularly a DNA encoding a protein or protein fragment according to the invention. An "isolated nucleic acid sequence" refers to a nucleic acid sequence which is no longer in the natural environment from which it was isolated, e.g. the nucleic acid sequence in a bacterial host cell or in the plant nuclear or plastid genome.

The terms "protein" or "polypeptide" are used interchangeably and refer to molecules consisting of a chain of amino acids, without reference to a specific mode of action, size, three-dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

The term "gene" means a DNA sequence comprising a region (transcribed region), which is transcribed into an RNA molecule (e.g. an mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites.

A "chimeric gene" (or recombinant gene) refers to any gene, which is not normally found in nature in a species, in particular a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense (reverse complement of the sense strand) or inverted repeat sequence (sense and antisense, whereby the RNA transcript forms double stranded RNA upon transcription).

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). An active protein in certain embodiments refers to a protein having a dominant-negative function due to a repressor domain being present. The coding sequence is preferably in sense-orientation and encodes a desired, biologically active protein or peptide, or an active peptide fragment. In gene silencing approaches, the DNA sequence is preferably present in the form of an antisense DNA or an inverted repeat DNA, comprising a short sequence of the target gene in antisense or in sense and antisense orientation. "Ectopic expression" refers to expression in a tissue in which the gene is normally not expressed.

A "transcription regulatory sequence" is herein defined as a nucleic acid sequence that is capable of regulating the rate of transcription of a (coding) sequence operably linked to the transcription regulatory sequence. A transcription regulatory sequence as herein defined will thus comprise all of the sequence elements necessary for initiation of transcription (promoter elements), for maintaining and for regulating transcription, including e.g. attenuators or enhancers. Although mostly the upstream (5') transcription regulatory sequences of a coding sequence are referred to, regulatory sequences found downstream (3') of a coding sequence are also encompassed by this definition.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two protein encoding regions, contiguous and in reading frame so as to produce a "chimeric protein". A "chimeric protein" or "hybrid protein" is a protein composed of various protein "domains" (or motifs) which is not found as such in nature but which a joined to form a functional protein, which displays the functionality of the joined domains (for example DNA binding or repression leading to a dominant negative function). A chimeric protein may also be a fusion protein of two or more proteins occurring in nature. The term "domain" as used herein means any part(s) or domain(s) of the protein with a specific structure or function that can be transferred to another protein for providing a new hybrid protein with at least the functional characteristic of the domain. Specific domains can also be used to identify protein members belonging to a group of similar transcription factors, such as orthologs from other plant species.

The term "target peptide" refers to amino acid sequences which target a protein to intracellular organelles such as plastids, preferably chloroplasts, mitochondria, or to the extracellular space (secretion signal peptide). A nucleic acid sequence encoding a target peptide may be fused (in frame) to the nucleic acid sequence encoding the amino terminal end (N-terminal end) of the protein.

A "nucleic acid construct" or "vector" is herein understood to mean a man-made nucleic acid molecule resulting from the use of recombinant DNA technology and which is used to deliver exogenous DNA into a host cell. The vector backbone may for example be a binary or superbinary vector (see e.g.

U.S. Pat. No. 5,591,616, US2002138879 and WO9506722), a co-integrate vector or a T-DNA vector, as known in the art and as described elsewhere herein, into which a chimeric gene is integrated or, if a suitable transcription regulatory sequence is already present, only a desired nucleic acid sequence (e.g. a coding sequence, an antisense or an inverted repeat sequence) is integrated downstream of the transcription regulatory sequence. Vectors usually comprise further genetic elements to facilitate their use in molecular cloning, such as e.g. selectable markers, multiple cloning sites and the like (see below).

A "host cell" or a "recombinant host cell" or "transformed cell" are terms referring to a new individual cell (or organism) arising as a result of at least one nucleic acid molecule, especially comprising a chimeric gene encoding a desired protein or a nucleic acid sequence which upon transcription yields an antisense RNA or an inverted repeat RNA (or hairpin RNA) for silencing of a target gene/gene family, having been introduced into said cell. The host cell is preferably a plant cell or a bacterial cell. The host cell may contain the nucleic acid construct as an extra-chromosomally (episomal) replicating molecule, or more preferably, comprises the chimeric gene integrated in the nuclear or plastid genome of the host cell.

The term "selectable marker" is a term familiar to one of ordinary skill in the art and is used herein to describe any genetic entity which, when expressed, can be used to select for a cell or cells containing the selectable marker. Selectable marker gene products confer for example antibiotic resistance, or more preferably, herbicide resistance or another selectable trait such as a phenotypic trait (e.g. a change in pigmentation) or nutritional requirements. The term "reporter" is mainly used to refer to visible markers, such as green fluorescent protein (GFP), eGFP, luciferase, GUS and the like.

The term "ortholog" of a gene or protein refers herein to the homologous gene or protein found in another species, which has the same function as the gene or protein, but (usually) diverged in sequence from the time point on when the species harbouring the genes diverged (i.e. the genes evolved from a common ancestor by speciation). Orthologs of an *Arabidopsis* gene may thus be identified in other plant species based on both sequence comparisons (e.g. based on percentages sequence identity over the entire sequence or over specific domains) and functional analysis.

The terms "homologous" and "heterologous" refer to the relationship between a nucleic acid or amino acid sequence and its host cell or organism, especially in the context of transgenic organisms. A homologous sequence is thus naturally found in the host species (e.g. a tomato plant transformed with a tomato gene), while a heterologous sequence is not naturally found in the host cell (e.g. a tomato plant transformed with a sequence from potato plants). Depending on the context, the term "homolog" or "homologous" may alternatively refer to sequences which are descendent from a common ancestral sequence (e.g. they may be orthologs).

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

"Sequence identity" and "sequence similarity" can be determined by alignment of two peptide or two nucleotide sequences using global or local alignment algorithms. Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length, maximizing the number of matches and minimises the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA. Alternatively percent similarity or identity may be determined by searching against databases such as FASTA, BLAST, etc.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids) are referred to.

DETAILED DESCRIPTION OF THE INVENTION

Using activation tagging, the inventors isolated and characterized an *Arabidopsis* gene, referred to as HARDY (HRD), the overexpression of which resulted in a number of changes in plant architecture and associated internal structures compared to the wild type. The activation of HRD resulted in leaves that are thicker in appearance, with a smaller compact hardy plant structure. The plant is more difficult to pull out of the ground, probably due to the enhanced lateral root network. The HRD gene was cloned and sequenced and was found to be similar to transcriptional factors defined as AP2/ERF (Alonso et al. 2003, Science 301, 653-657). However no functions of HRD have been described and no uses for the HRD gene suggested in the art.

Constitutive expression of the HRD gene in transgenic *Arabidopsis* plants showed the same phenotype as the original activation tag line, although the phenotype was more severe. The original overexpression mutant hrd was tested for resistance to abiotic and biotic stress conditions and was found to be significantly more resistant than wild-type controls. In addition a conditional overexpression strategy, using a HRD fusion to a glucorticoid receptor, showed the phenotype can be induced and plants with mild or almost no phenotype were resistant to the stress tests. Microarray experiments of the hrd mutant, using whole genome *Arabidopsis* microarrays, showed differential expression of a set of genes that were different from that of overexpression of the other known stress resistant AP2/ERF genes like DREB1A, indicating a different mechanism in conferring general stress resistance.

Nucleic Acid Sequences and Proteins According to the Invention

In one embodiment of the invention nucleic acid sequences and amino acid sequences of members of the HARDY transcription factor are provided, as well as methods for isolating or identifying orthologs of the HARDY gene in other plant species.

The function of a protein can be tested using a variety of known methods, preferably by comparing the phenotype of transformants constitutively expressing the protein being tested to the phenotype of HRD over-expressing transformants of the same host species (and variety) (preferably comprising a chimeric HRD encoding gene stably integrated into the host's genome), allowing a direct comparison of the functional effect on the phenotype of the transformants. It is understood that in any transformation experiments a certain degree of variation in the phenotype of transformants is seen, normally due to position effects in the genome and/or due to copy number. A skilled person will know how to compare transformants to one another, e.g. by selecting single copy number events and analysing their phenotypes. Other methods of determining or confirming in vivo gene/protein function include the generation of knock-out mutants or transient expression studies. Promoter-reporter gene expression studies may also provide information as to the spatio-temporal expression pattern and the role of the protein.

Constitutive (over)expression of the HARDY gene member results in one or more of the following phenotypic changes compared to the wild type or control transformants:
  Thicker leaves with an increased layer mesophyll layer
  Smaller compact and hardy looking plant
  Stronger root structure with enhanced lateral roots
  Increased resistance to a pathogen, e.g. non-race specific (*Verticillium*)
  Enhanced tolerance to drought as revealed by higher survival than wild-type These phenotypes can be utilized in creating transgenic plants or plant tissues/organs with modified and improved agronomical characteristics; such as enhanced drought tolerance and others as described elsewhere herein.

In one embodiment the invention provides a transgenic crop plant comprising integrated in its genome a chimeric gene, characterized by said chimeric gene comprising a transcription regulatory sequence active in plant cells operably linked to a nucleic acid sequence encoding a protein having the sequence of SEQ ID NO: 3 or a protein at least 70% identical to SEQ ID NO: 3, or an ortholog protein or a functional fragment thereof.

Preferably the plant has one or more of the phenotypes selected from the group consisting of: enhanced drought tolerance, enhanced disease resistance and enhanced root structure.

In a further preferred embodiment said transcription regulatory sequence is selected from the group consisting of: a constitutive promoter, a inducible promoter, a tissue-specific promoter and a developmentally regulated promoter.

In another embodiment the invention provides a seed or a fruit of the transgenic plant.

In a further embodiment the invention provides a chimeric gene comprising a tissue specific-, inducible- or developmentally regulated promoter active in plant cells, operably linked to a nucleic acid sequence encoding a protein having the sequence of SEQ ID NO: 3 or a protein at least 70% identical to SEQ ID NO: 3, or an ortholog protein or a functional fragment thereof.

Also provided is a vector comprising said chimeric gene.

Preferably the encoding nucleic acid sequence comprised in the vector has the sequence of SEQ ID NO: 1. Further it is preferred that the encoding nucleic acid sequence is operably linked with a stress inducible promoter.

In a further embodiment the invention provides the use of 4 nucleic acid sequence encoding a protein having the sequence of SEQ ID NO: 3 or a protein at least 70% identical to SEQ ID NO: 3, or an ortholog protein or a functional fragment thereof for the generation of transgenic plants with enhanced drought tolerance, enhanced disease resistance and/or enhanced root structure.

Other members similar to HARDY can be identified in silico, e.g. by identifying nucleic acid or protein sequences in existing nucleic acid or protein database (e.g. GENBANK, SWISSPROT, TrEMBL) and using standard sequence analysis software, such as sequence similarity search tools (BLASTN, BLASTP, BLASTX, TBLAST, PASTA, etc.).

The HRD proteins according to the invention, example provided as SEQ ID NO: 3, may be isolated from natural sources, synthesized de novo by chemical synthesis (using e.g. a peptide synthesizer such as supplied by Applied Biosystems) or produced by recombinant host cells. The HRD proteins according to the invention may be used to raise mono- or polyclonal antibodies, which may for example be used for the detection of HRD proteins in samples (immunochemical analysis methods and kits).

Chimeric or hybrid HRD proteins comprise segments of the AP2 domain and other parts of the HRD protein. Domains may be exchanged (domain swapping) between HRD proteins and other unrelated proteins, as long as the functionality of the resulting chimeric protein is essentially similar to that of HRD. A chimeric HRD protein may thus, for example, comprise the HRD protein, including, the AP2 domain and in addition one or more protein domains not normally found in HRD proteins, such as stabilizing domains, binding domains (e.g. hormone binding domains, such as found in the glucocorticoid receptor, resulting in inducibility), etc. In another embodiment chimeric HRD proteins are provided which comprise a HRD-repressor domain fusion, such as the HRD-EAR fusion described below. In transgenic plants, overexpression of these chimeric proteins result in a dominant negative phenotype. HRD-repressor domain fusion may also comprise additional domains fused thereto, such as e.g. a hormone binding domain (see e.g. Markel et al. 2002, Nucl. Acid Res. 30, 4709-4719).

Also provided are nucleic acid sequences (genomic DNA, cDNA, RNA) encoding HRD protein, such as for example HRD, as defined above (including any chimeric or hybrid HRD proteins), or any HRD protein from another species. Due to the degeneracy of the genetic code various nucleic acid sequences may encode the same amino acid sequence. The nucleic acid sequences provided include naturally occurring, artificial or synthetic nucleic acid sequences. Example of nucleic acid sequence encoding HRD is provided for in SEQ ID NO: 1 (sequence coding for HRD protein from *Arabidopsis*) and SEQ ID NO: 2 (genomic HRD sequence from *Arabidopsis*). It is understood that when sequences are depicted in as DNA sequences while RNA is referred to, the actual base sequence of the RNA molecule is identical with the difference that thymine (T) is replace by uracil (U).

It is clear that many methods can be used to identify, synthesise or isolate variants or fragments of HRD nucleic acid sequences, such as nucleic acid hybridization, PCR technology, in silico analysis and nucleic acid synthesis, and the like.

The nucleic acid sequence, particularly DNA sequence, encoding the HRD proteins of this invention can be inserted in expression vectors to produce high amounts of HRD proteins (or e.g. chimeric HRD proteins), as described below. For optimal expression in a host the HRD DNA sequences can be codon-optimized by adapting the codon usage to that most preferred in plant genes, particularly to genes native to the plant genus or species of interest (Bennetzen & Hall, 1982, J. Biol. Chem. 257, 3026-3031; Itakura et al., 1977 Science 198, 1056-1063.) using available codon usage tables (e.g. more adapted towards expression in cotton, soybean corn or rice). Codon usage tables for various plant species are published for example by Ikemura (1993, In "Plant Molecular Biology Labfax", Croy, ed., Bios Scientific Publishers Ltd.) and Nakamura et al. (2000, Nucl. Acids Res. 28, 292.) and in the major DNA sequence databases (e.g. EMBL at Heidelberg, Germany). Accordingly, synthetic DNA sequences can be constructed so that the same or substantially the same proteins are produced. Several techniques for modifying the codon usage to that preferred by the host cells can be found in patent and scientific literature. The exact method of codon usage modification is not critical for this invention.

Small modifications to a DNA sequence such as described above can be routinely made, i.e., by PCR-mediated mutagenesis (Ho et al., 1989, Gene 77, 51-59., White et al., 1989, Trends in Genet. 5, 185-189). More profound modifications to a DNA sequence can be routinely done by de novo DNA synthesis of a desired coding region using available techniques.

Also, the HRD nucleic acid sequences can be modified so that the N-terminus of the HRD protein has an optimum translation initiation context, by adding or deleting one or more amino acids at the N-terminal end of the protein. Often it is preferred that the proteins of the invention to be expressed in plants cells start with a Met-Asp or Met-Ala dipeptide for optimal translation initiation. An Asp or Ala codon may thus be inserted following the existing Met, or the second codon, Val, can be replaced by a codon for Asp (GAT or GAC) or Ala (GCT, GCC, GCA or GCG). The DNA sequences may also be modified to remove illegitimate splice sites.

In one embodiment of the invention HRD gene expression is downregulated in a host cell, plant or specific tissue(s), by e.g. RNAi approaches, as described elsewhere. In yet another embodiment HRD loss-of-function phenotypes (of host cells, tissues or whole plants) are generated by expressing a nucleic acid sequence encoding a protein fusion of a HRD protein (as defined) with a (dominant) repressor domain. "Loss-of-function" refers herein to the loss of HRD protein function in a host tissue or organisms, and encompasses the function at the molecular level (e.g. loss of transcriptional activation of downstream target genes of the HRD transcription factor) and preferably also at the phenotypic level. For example, in order to provide loss-of-function, HRD protein fusions are made with a 12 amino acid 'EAR' repressor domain as described by Hiratsu et al., 2003 (Plant J. 34:733-739), incorporated herein by reference. These repressor domain fusions to any one of the HRD proteins (as defined), termed herein 'HRD-EAR' fusion proteins, are able to cause repression of the downstream target genes and thus result in an effective loss-of-function mutant (dominant negative effect). These repressor fusions also effect repression in heterologous plants where the orthologous genes have not yet been identified. In one embodiment a nucleic acid sequence is provided which encodes a chimeric repressor domain-HRD protein fusion protein, especially a HRD-EAR fusion protein. In addition a vector comprising said nucleic acid sequence and a host cell, tissue and/or organism comprising the chimeric gene is provided. To generate a HRD-repressor domain fusion protein, the nucleic acid sequence encoding the repressor domain is translationally fused to the nucleic acid sequence comprising the HRD coding sequence. The HRD-repressor domain fusion protein encoding nucleic acid sequence (especially HRD-EAR) is placed under control of constitutive or specific promoters (e.g. tissue specific or developmentally regulated). Constitutive expression provides a loss-of-function in all host tissues where HRD or orthologs are expressed and required for function. Specific expression of the HRD-EAR protein provides a loss-of-function in the specific tissue or condition, e.g. when a specific promoter is operably linked to a nucleic acid encoding a HRD-EAR fusion protein.

It is understood that HRD proteins may be operably fused to other repression domains available in the art which function in plant cells. These include repressor domains of animal proteins, such as the *Drosophila* ENGRAILED (En) repressor domain. For example the N-terminal 298 amino acids may be fused to a HRD protein according to the invention, creating a dominant-negative chimeric protein (see Markel et al. 2002, Nucleic Acid Research Vol 30, 4709-4719 and Chandler and Werr 2003, Trends in Plant Science Vol. 8, 279-285, both incorporated by reference). It is noted that repressor domains may be fused to the HRD protein at the C-terminus or at the N-terminus, depending on the domain. The nucleic acid sequence encoding the dominant-negative fusion protein may be referred to as a "dominant-negative chimeric gene" and when transferred into a host genome as a "dominant-negative transgene" (either stably integrated in the host genome or transiently expressed). Other plant repressor domains are for example the LEUNG and SEUSS co-repressors of AGAMOUS, FLC and polycomb proteins. Other animal repressor domains include for example the WT1, eve, c-ErbA and v-ErbA and Krüppel associated box (see Chandler and Werr, 2003, supra and references therein).

In another embodiment of the invention PCR primers and/or probes and kits for detecting the HRD DNA sequences are provided. Degenerate or specific PCR primer pairs to amplify HRD DNA from samples can be synthesized based on SEQ ID NO 3 as known in the art (see Dieffenbach and Dveksler (1995) PCR Primer: A Laboratory Manual, Cold Spring Harbor Laboratory Press, and McPherson at al. (2000) PCR-Basics: From Background to Bench, First Edition, Springer Verlag, Germany). Likewise, DNA fragments of SEQ ID NO's 1-2 can be used as hybridization probes. An HRD detection kit may comprise either HRD specific primers and/or HRD specific probes, and an associated protocol to use the primers or probe to detect HRD DNA in a sample. Such a detection kit may, for example, be used to determine, whether a plant has been transformed with an HRD gene (or part thereof) of the invention. Because of the degeneracy of the genetic code, some amino acid codons can be replaced by others without changing the amino acid sequence of the protein.

In another embodiment antibodies that bind specifically to a HRD protein according to the invention are provided. In particular monoclonal or polyclonal antibodies that bind to HRD or to fragments or variants thereof, are encompassed herein. An antibody can be prepared by using a HRD protein according to the invention as an antigen in an animal using methods known in the art, as e.g. described in Harlow and Lane "Using Antibodies: A laboratory manual" (New York: Cold Spring Harbor Press 1998) and in Liddell and Cryer "A Practical Guide to Monoclonal Antibodies" (Wiley and Sons, 1991). The antibodies can subsequently be used to isolate, identify, characterize or purify the HRD protein to which it binds, for example to detect the HRD protein in a sample, allowing the formation of an immunocomplex and detecting the presence of the immunocomplex by e.g. ELISA (enzyme linked immunoassay) or immunoblot analysis. Also provided are immunological kits, useful for detecting the HRD proteins, protein fragments or epitopes in a sample provided. Samples may be cells, cell supernatants, cell suspensions, tissues, etc. Such a kit comprises at least an antibody that binds to a HRD protein and one or more immunodetection reagents. The antibodies can also be used to isolate/identify other HRD proteins, for example by ELISA or Western blotting.

In addition, nucleic acid sequences comprising the HRD promoter is provided herein. The transcription regulatory sequences are found in the about 1 kb sequence upstream of the ATG codon of SEQ ID NO: 1. The transcription regulatory sequence of HRD is provided herein in SEQ ID NO: 2, as the 5' region of 1.1 kb. These transcription regulatory sequences may be used for the construction of chimeric genes and for expressing operably linked nucleic acid sequences in hosts or host cells. Especially the HRD transcription regulatory sequence may be used for expression in seed and embryo for expression of genes for early stress tolerance. It is understood that the tissue specificity of the transcription regulatory sequences can be improved or specified by analysing deletion fragments of the sequences provided for their ability to direct expression of nucleic acid sequences operably linked thereto. Such deletion analysis allows the removal of nucleic acid parts which cause non-specific (background) expression. Similarly, the transcription regulatory sequences of other HRD-like genes can be isolated by sequencing the genomic DNA upstream of the ATG codon, using known methods such as TAIL-PCR.

Chimeric Genes, Vectors and Recombinant Microorganisms According to the Invention In one embodiment of the invention nucleic acid sequences encoding HRD proteins (including e.g. fusion proteins such as HRD-GR and HRD-EAR), as described above, are used to make chimeric genes, and vectors comprising these for transfer of the chimeric gene into a host cell and production of the HRD protein(s) in host cells, such as cells, tissues, organs or organisms derived from transformed cell(s). Host cells are preferably plant cells and, but microbial hosts (bacteria, yeast, fungi, etc.) are also envisaged. Any crop plant may be a suitable host, such as monocotyledonous plants or dicotyledonous plants, for example maize/corn (*Zea* species, e.g. *Z. mays*, *Z. diploperennis* (chapule), *Zea luxurians* (Guatemalan teosinte), *Zea mays* subsp. *huehuetenangensis* (San Antonio Huista teosinte), *Z. mays* subsp. *mexicana* (Mexican teosinte), *Z. mays* subsp. *parviglumis* (Balsas teosinte), *Z. perennis* (perennial teosinte) and *Z. ramosa*), wheat (*Triticum* species), barley (e.g. *Hordeum vulgare*), oat (e.g. *Avena sativa*), sorghum (*Sorghum bicolor*), rye (*Secale cereale*), soybean (*Glycine* spp, e.g. *G. max*), cotton (*Gossypium* species, e.g. *G. hirsutum*, *G. barbadense*), *Brassica* spp. (e.g. *B. napus*, *B. juncea*, *B. oleracea*, *B. rapa*, etc), sunflower (*Helianthus annus*), tobacco (*Nicotiana* species), alfalfa (*Medicago sativa*), rice (*Oryza* species, e.g. *O. sativa indica* cultiargroup or *japonica* cultivar-group), forage grasses, pearl millet (*Pennisetum* spp. e.g. *P. glaucum*), tree species, vegetable species, such as *Lycopersicon* ssp (e.g. *Lycopersicon esculentum*), potato (*Solanum tuberosum*, other *Solanum* species), egg-plant (*Solanum melongena*), peppers (*Capsicum annuum*, *Capsicum frutescens*), pea, bean (e.g. *Phaseolus* species), fleshy fruit (grapes, peaches, plums, strawberry, mango), ornamental species (e.g. Rose, Petunia, Chrysanthemum, Lily, Gerbera species), woody trees (e.g. species of *Populus*, *Salix*, *Quercus*, *Eucalyptus*), fibre species e.g. flax (*Linum usitatissimum*) and hemp (*Cannabis sativa*).

A "crop plant" refers herein to a plant species which is cultivated and bred by humans for specific purposes. A crop plant may be cultivated for food purposes (e.g. field crops), or for ornamental purposes (e.g. production of flowers for cutting, grasses for lawns, etc.). A crop plant as defined herein also includes plants from which non-food products are harvested, such as oil for fuel, plastic polymers, pharmaceutical products, cork and the like.

The construction of chimeric genes and vectors for, preferably stable, introduction of HRD protein encoding nucleic acid sequences into the genome of host cells is generally known in the art. To generate a chimeric gene the nucleic acid sequence encoding a HRD protein (or e.g. a HRD-GR domain fusion protein) is operably linked to a promoter sequence, suitable for expression in the host cells, using standard molecular biology techniques. The promoter sequence may already be present in a vector so that the HRD nucleic sequence is simply inserted into the vector downstream of the promoter sequence. The vector is then used to transform the host cells and the chimeric gene is inserted in the nuclear genome or into the plastid, mitochondrial or chloroplast genome and expressed there using a suitable promoter (e.g., Mc Bride et al., 1995 Bio/Technology 13, 362; U.S. Pat. No. 5,693,507). In one embodiment a chimeric gene comprises a suitable promoter for expression in plant cells or microbial cells (e.g. bacteria), operably linked thereto a nucleic acid sequence encoding a HRD protein or fusion protein according to the invention, optionally followed by a 3' nontranslated nucleic acid sequence.

The HRD nucleic acid sequence, preferably the HRD chimeric gene, encoding a functional HRD protein (or in certain embodiments a functional HRD-GR domain fusion protein), can be stably inserted in a conventional manner into the nuclear genome of a single plant cell, and the so-transformed plant cell can be used in a conventional manner to produce a transformed plant that has an altered phenotype due to the presence of the HRD protein in certain cells at a certain time. In this regard, a T-DNA vector, comprising a nucleic acid sequence encoding a HRD protein, in *Agrobacterium tumefaciens* can be used to transform the plant cell, and thereafter, a transformed plant can be regenerated from the transformed plant cell using the procedures described, for example, in EP 0116718, EP 0270822, PCT publication WO84/02913 and published European Patent application EP 0242246 and in Gould et al. (1991, Plant Physiol. 95, 426-434). The construction of a T-DNA vector for *Agrobacterium* mediated plant transformation is well known in the art: The T-DNA vector may be either a binary vector as described in EP 0120561 and EP 0120515 or a co-integrate vector which can integrate into the *Agrobacterium* Ti-plasmid by homologous recombination, as described in EP 0116718.

Preferred T-DNA vectors each contain a promoter operably linked to HRD encoding nucleic acid sequence between T-DNA border sequences, or at least located to the left of the right border sequence. Border sequences are described in Gielen et al. (1984, EMBO J. 3,835-845). Of course, other types of vectors can be used to transform the plant cell, using procedures such as direct gene transfer (as described, for example in EP 0223247), pollen mediated transformation (as described, for example in EP 0270356 and WO85/01856), protoplast transformation as, for example, described in U.S. Pat. No. 4,684,611, plant RNA virus-mediated transformation (as described, for example in EP 0067553 and U.S. Pat. No. 4,407,956), liposome-mediated transformation (as described, for example in U.S. Pat. No. 4,536,475), and other methods such as those described methods for transforming certain lines of corn (e.g., U.S. Pat. No. 6,140,553; Fromm et al., 1990, Bio/Technology 8, 833-839; Gordon-Kamm et al., 1990, The Plant Cell 2, 603-618) and rice (Shimamoto et al., 1989, Nature 338, 274-276; Datta et al. 1990, Bio/Technology 8, 736-740) and the method for transforming monocots generally (PCT publication WO92/09696). For cotton transformation see also WO 00/71733, and for rice transformation see also the methods described in WO92/09696, WO94/00977 and WO95/06722. For sorghum transformation see e.g. Jeoung J M et al. 2002, Hereditas 137: 20-8 or Zhao Z Y et al. 2000, Plant Mol Biol. 44:789-98). Likewise, selection and regeneration of transformed plants from transformed cells is well known in the art. Obviously, for different species and even for different varieties or cultivars of a single species, protocols are specifically adapted for regenerating transformants at high frequency.

Besides transformation of the nuclear genome, also transformation of the plastid genome, preferably chloroplast genome, is included in the invention. One advantage of plastid genome transformation is that the risk of spread of the transgene(s) can be reduced. Plastid genome transformation can be carried out as known in the art, see e.g. Sidorov V A et al. 1999, Plant J. 19: 209-216 or Lutz K A at al. 2004, Plant J. 37(6):906-13.

The resulting transformed plant can be used in a conventional plant breeding scheme to produce more transformed plants with the same characteristics or to introduce the gene part into other varieties of the same or related plant species. Seeds, which are obtained from the transformed plants, contain the chimeric HRD gene as a stable genomic insert. Cells of the transformed plant can be cultured in a conventional manner to produce the HRD protein, which can be recovered for other use e.g. antibody production.

The HRD nucleic acid sequence is inserted in a plant cell genome so that the inserted coding sequence is downstream (i.e. 3') of, and under the control of, a promoter which can direct the expression in the plant cell. This is preferably accomplished by inserting the chimeric gene in the plant cell genome, particularly in the nuclear or plastid (e.g. chloroplast) genome.

Preferred promoters include: the strong constitutive 35S promoters or enhanced 35S promoters (the "35S promoters") of the cauliflower mosaic virus (CaMV) of isolates CM 1841 (Gardner et al., 1981, Nucleic Acids Research 9, 2871-2887), CabbB-S (Franck et al., 1980, Cell 21, 285-294) and CabbB-JI (Hull and Howell, 1987, Virology 86, 482-493); the 35S promoter described by Odell et al. (1985, Nature 313, 810-812) or in U.S. Pat. No. 5,164,316, promoters from the ubiquitin family (e.g. the maize ubiquitin promoter of Christensen et al., 1992, Plant Mol. Biol. 18, 675-689, EP 0 342 926, see also Cornejo et al. 1993, Plant Mol. Biol. 23, 567-581), the gos2 promoter (de Pater et al., 1992 Plant J. 2, 834-844), the emu promoter (Last et al., 1990, Theor. Appl. Genet. 81, 581-588), Arabidopsis actin promoters such as the promoter described by An et al. (1996, Plant J. 10, 107.), rice actin promoters such as the promoter described by Zhang et al. (1991, The Plant Cell 3, 1155-1165) and the promoter described in U.S. Pat. No. 5,641,876 or the rice actin 2 promoter as described in WO070067; promoters of the Cassaya vein mosaic virus (WO 97/48819, Verdaguer et al. 1998, Plant Mol. Biol. 37, 1055-1067), the pPLEX series of promoters from Subterranean Clover Stunt Virus (WO 96/06932, particularly the S7 promoter), a alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T-DNA (Velten et al., 1984, EMBO J. 3, 2723-2730), the Figwort Mosaic Virus promoter described in U.S. Pat. No. 6,051,753 and in EP426641, his-tone gene promoters, such as the Ph4a748 promoter from Arabidopsis (PMB 8: 179-191), or others.

Alternatively, a promoter can be utilized which is not constitutive but rather is specific for one or more tissues or organs of the plant (tissue preferred/tissue specific, including developmentally regulated promoters), for example leaf preferred, epidermis preferred, root preferred, flower tissue e.g. tapetum or anther preferred, seed preferred, pod preferred, etc., whereby the HRD gene (including e.g. the HRD-GR fusion protein encoding gene) is expressed only in cells of the specific tissue(s) or organ(s) and/or only during a certain developmental stage. For example, the HRD gene(s) can be selectively expressed in the leaves of a plant by placing the coding sequence under the control of a light-inducible promoter such as the promoter of the ribulose-1,5-bisphosphate carboxylase small subunit gene of the plant itself or of another plant, such as pea, as disclosed in U.S. Pat. No. 5,254,799 or Arabidopsis as disclosed in U.S. Pat. No. 5,034,322. The choice of the promoter is determined by the phenotype one aims to achieve, as will be described in more detail below.

To achieve drought tolerance a constitutive, a root specific, stress inducible or pathogen inducible promoter would be suitable. A suitable abiotic stress inducible promoter would be the rd29A promoter (Kasuga et al 1999).

For expression in root tissue a promoter preferentially active in roots is described in WO00/29566. Another promoter for root preferential expression is the ZRP promoter (and modifications thereof) as described in U.S. Pat. No. 5,633,363. Another root specific promoter is provided in this embodiment as the BOUNTIFUL promoter (Pereira et al, unpublished).

Another alternative is to use a promoter whose expression is inducible. Examples of inducible promoters are wound-inducible promoters, such as the MPI promoter described by Cordera et al. (1994, The Plant Journal 6, 141), which is induced by wounding (such as caused by insect or physical wounding), or the COMPTII promoter (WO0056897) or the promoter described in U.S. Pat. No. 6,031,151. Alternatively the promoter may be inducible by a chemical, such as dexamethasone as described by Aoyama and Chua (1997, Plant Journal 11: 605-612) and in U.S. Pat. No. 6,063,985 or by tetracycline (TOPFREE or TOP 10 promoter, see Gatz, 1997, Annu Rev Plant Physiol Plant Mol. Biol. 48: 89-108 and Love et al. 2000, Plant J. 21: 579-88). Other inducible promoters are for example inducible by a change in temperature, such as the heat shock promoter described in U.S. Pat. No. 5,447,858, by anaerobic conditions (e.g. the maize ADH1S promoter), by light (U.S. Pat. No. 6,455,760), by pathogens (e.g. EP759085 or EP309862) or by senescence (SAG12 and SAG13, see U.S. Pat. No. 5,689,042). Obviously, there are a range of other promoters available.

The HRD coding sequence (or a chimeric HRD protein encoding sequence) is inserted into the plant genome so that the coding sequence is upstream (i.e. 5') of suitable 3' end transcription regulation signals ("3' end") (i.e. transcript formation and polyadenylation signals). Polyadenylation and transcript formation signals include those of the CaMV 35S gene ("3' 35S"), the nopaline synthase gene ("3' nos") (Depicker et al., 1982 J. Molec. Appl. Genetics 1, 561-573.), the octopine synthase gene ("3' ocs") (Gielen et al., 1984, EMBO J. 3, 835-845) and the T-DNA gene 7 ("3' gene 7") (Velten and Schell, 1985, Nucleic Acids Research 13, 6981-6998), which act as 3'-untranslated DNA sequences in transformed plant cells, and others.

Introduction of the T-DNA vector into *Agrobacterium* can be carried out using known methods, such as electroporation or triparental mating.

A HRD encoding nucleic acid sequence can optionally be inserted in the plant genome as a hybrid gene sequence whereby the HRD sequence is linked in-frame to a (U.S. Pat. No. 5,254,799; Vaeck et al., 1987, Nature 328, 33-37) gene encoding a selectable or scorable marker, such as for example the neo (or nptII) gene (EP 0 242 236) encoding kanamycin resistance, so that the plant expresses a fusion protein which is easily detectable.

Transformation of plant cells can also be used to produce the HRD protein(s) of the invention in large amounts in plant cell cultures that are resistant to a number of stresses and can be utilized for production of specific products in culture. When reference to a transgenic plant cell is made herein, this refers to a plant cell (or also a plant protoplast) as such in isolation or in tissue culture, or to a plant cell (or protoplast) contained in a plant or in a differentiated organ or tissue, and both possibilities are specifically included herein. Hence, a reference to a plant cell in the description or claims is not meant to refer only to isolated cells in culture, but refers to any plant cell, wherever it may be located or in whatever type of plant tissue or organ it may be present.

All or part of a HRD nucleic acid sequence, encoding a HRD protein (or a chimeric HRD protein), can also be used to transform microorganisms, such as bacteria (e.g. *Escherichia coli, Pseudomonas, Agrobacterium, Bacillus*, etc.), fungi, viruses, algae or insects. Transformation of bacteria, with all or part of a HRD nucleic acid sequence of this invention, incorporated in a suitable cloning vehicle, can be carried out in a conventional manner, preferably using conventional electroporation techniques as described in Maillon et al. (1989, FEMS Microbiol. Letters 60, 205-210.) and WO 90/06999. For expression in prokaryotic host cell, the codon usage of the nucleic acid sequence may be optimized accordingly (as described for plants above). Intron sequences should be removed and other adaptations for optimal expression may be made as known.

For obtaining enhanced expression in monocot plants such as grass species, e.g. corn or rice, an intron, preferably a monocot intron, can be added to the chimeric gene. For example the insertion of the intron of the maize Adhi gene into the 5' regulatory region has been shown to enhance expression in maize (Callis et. al., 1987, Genes Develop. 1: 1183-1200). Likewise, the HSP70 intron, as described in U.S. Pat. No. 5,859,347, may be used to enhance expression. The DNA sequence of the HRD nucleic acid sequence can be further changed in a translationally neutral manner, to modify possibly inhibiting DNA sequences present in the gene part by means of site-directed intron insertion and/or by introducing changes to the codon usage, e.g., adapting the codon usage to that most preferred by plants, preferably the specific relevant plant genus, as described above.

In accordance with one embodiment of this invention, the HRD proteins (or chimeric proteins) are targeted to intracellular organelles such as plastids, preferably chloroplasts, mitochondria, or are secreted from the cell, potentially optimizing protein stability and/or expression. Similarly, the protein may be targeted to vacuoles. For this purpose, in one embodiment of this invention, the chimeric genes of the invention comprise a coding region encoding a signal or target peptide, linked to the HRD protein coding region of the invention. Particularly preferred peptides to be included in the proteins of this invention are the transit peptides for chloroplast or other plastid targeting, especially duplicated transit peptide regions from plant genes whose gene product is targeted to the plastids, the optimized transit peptide of Capellades et al. (U.S. Pat. No. 5,635,618), the transit peptide of ferredoxin-NADP+oxidoreductase from spinach (Oelmuller et. al., 1993, Mol. Gen. Genet. 237, 261-272), the transit peptide described in Wong et al. (1992, Plant Molec. Biol. 20, 81-93) and the targeting peptides in published PCT patent application WO 00/26371. Also preferred are peptides signalling secretion of a protein linked to such peptide outside the cell, such as the secretion signal of the potato proteinase inhibitor 11 (Keil et al., 1986, Nucl. Acids Res. 14, 5641-5650), the secretion signal of the alpha-amylase 3 gene of rice (Sutliff et al., 1991, Plant Molec. Biol. 16, 579-591) and the secretion signal of tobacco PR1 protein (Cornelissen et al., 1986, EMBO J. 5, 37-40). Particularly useful signal peptides in accordance with the invention include the chloroplast transit peptide (e.g. Van Den Broeck et al., 1985, Nature 313, 358), or the optimized chloroplast transit peptide of U.S. Pat. No. 5,510,471 and U.S. Pat. No. 5,635,618 causing transport of the protein to the chloroplasts, a secretory signal peptide or a peptide targeting the protein to other plastids, mitochondria, the ER, or another organelle. Signal sequences for targeting to intracellular organelles or for secretion outside the plant cell or to the cell wall are found in naturally targeted or secreted proteins, preferably those described by Klosgen et al. (1989, Mol. Gen. Genet. 217, 155-161), Klosgen and Weil (1991, Mol. Gen. Genet. 225, 297-304), Neuhaus & Rogers (1998, Plant Mol. Biol. 38, 127-144), Bih et al. (1999, J. Biol. Chem. 274, 22884-22894), Morris et al. (1999, Biochem. Biophys. Res. Commun. 255, 328-333), Hesse et al. (1989, EMBO J. 8, 2453-2461), Tavladoraki et al. (1998, FEBS Lett. 426, 62-66.), Terashima et al. (1999, Appl. Microbiol. Biotechnol. 52, 516-523), Park et al. (1997, J. Biol. Chem. 272, 6876-6881), Shcherban et al. (1995, Proc. Natl. Acad. Sci. USA 92, 9245-9249).

To allow secretion of the HRD proteins to the outside of the transformed host cell, an appropriate secretion signal peptide may be fused to the amino terminal end (N-terminal end) of the HRD protein. Putative signal peptides can be detected using computer based analysis, using programs such as the program Signal Peptide search (SignalP V1.1 or 2.0) (Von Heijne, Gunnar, 1986 and Nielsen et al., 1996).

In one embodiment, several HRD encoding nucleic acid sequences are co-expressed in a single host. A co-expressing host plant is easily obtained by transforming a plant already expressing HRD protein of this invention, or by crossing plants transformed with different HRD proteins of this invention. Alternatively, several HRD protein encoding nucleic acid sequences can be present on a single transformation vector or be co-transformed at the same time using separate vectors and selecting transformants comprising both chimeric genes. Similarly, one or more HRD encoding genes may be expressed in a single plant together with other chimeric genes, for example encoding other proteins which enhance drought tolerance, such as CBF1, DREB1A, the rice OsDREB genes (Dubouzet et al, 2003, Plant J. 33: 751), the SHINE genes (Aharoni et al 2004, Plant Cell 16: 2463-80) or others.

It is understood that the different proteins can be expressed in the same plant, or each can be expressed in a single plant and then combined in the same plant by crossing the single plants with one another. For example, in hybrid seed production, each parent plant can express a single protein. Upon crossing the parent plants to produce hybrids, both proteins are combined in the hybrid plant.

Preferably, for selection purposes but also for weed control options, the transgenic plants of the invention are also transformed with a DNA encoding a protein conferring resistance to herbicide, such as a broad-spectrum herbicide, for example herbicides based on glufosinate ammonium as active ingredient (e.g. Liberty® or BASTA; resistance is conferred by the PAT or bar gene; see EP 0242236 and EP 0242246) or glyphosate (e.g. Roundup®; resistance is conferred by EPSPS genes, see e.g. EP0508909 and EP 0507698). Using herbicide resistance genes (or other genes conferring a desired phenotype) as the selectable marker further has the advantage that the introduction of antibiotic resistance genes can be avoided.

Alternatively, other selectable marker genes may be used, such as antibiotic resistance genes. As it is generally not accepted to retain antibiotic resistance genes in the transformed host plants, these genes can be removed again following selection of the transformants. Different technologies exist for removal of transgenes. One method to achieve removal is by flanking the chimeric gene with lox sites and, following selection, crossing the transformed plant with a CRE recombinase-expressing plant (see e.g. EP506763B1). Site specific recombination results in excision of the marker gene. Another site specific recombination systems is the FLP/FRT system described in EP686191 and U.S. Pat. No. 5,527, 695. Site specific recombination systems such as CRE/LOX and FLP/FRT may also be used for gene stacking purposes. Further, one-component excision systems have been described, see e.g. WO9737012 or WO9500555).

Transformed Plant Cells/Plants/Seeds and Uses of the Nucleic Acid Sequence and Proteins According to the Invention In the following part the use of the HRD sequences according to the invention to generate transgenic plant cells, plants, plant seeds and any derivatives/progeny thereof, with one or more modified phenotypes is described.

A) Plants with Enhanced Stress Tolerance

A transgenic, stress tolerant plant can be generated by transforming a plant host cell with a nucleic acid sequence encoding the HRD protein under the control of a suitable promoter, as described above, and regenerating a transgenic plant from said cell. Preferred promoters are promoters which are induced specifically by stresses (abiotic and biotic) or following application of chemical compounds. In particular the following promoters are preferred:

Rice PR10 promoter (Hashimoto et al, 2004, Plant Cell Physiol. 45: 550-559)

*Arabidopsis* AtPLA IIA promoter (Narusaka et al, 2003, Plant Cell Physiol. 44: 1246-52)

*Arabidopsis* CYP83B1 promoter (Narusaka et al. 2004, PMB 55: 327-342)

Wheat germin gf-2.8 promoter (Berna & Bernier, 1999, PMB 39: 539-549)

"Drought tolerance" or "increased/enhanced drought tolerance" is used herein to refer to an enhanced ability of transformants (compared to wild type or control transformants) to tolerate a period of drought (water deprivation/depletion leading to e.g. visible leaf wilting symptoms in control plants) and to recover subsequently, thereby leading to a reduced overall yield loss, as more plants per $m^2$ survive and/or the yield of the surviving plants is not significantly reduced. Drought tolerance can be assessed in controlled environments (green house or growth chambers) by placing at least about 10 transformants per transformation event and at least 10 control plants for various time periods (ranging from 1-4 weeks or more) into the environment without watering them, until leaf wilting or loss of turgor is caused on control plants, and subsequently watering the plants again for 1-2 weeks, while their recovery phenotype is analyzed. Transfomants with drought tolerance survive at least 2, 3, 4, 5, 6, 7 days, preferably at least 2-5 days longer without water than control-transformants (e.g. transformed with an empty vector) or wild type plants do under the same conditions, and which show irreversible tissue damage. In another method of estimating tolerance the recovery of transformants is at least about 2-5 times higher than that of the control plants (e.g. with 20% control recovery, 40-100% survival in transformants).

"Disease resistance" or "enhanced disease resistance" is used herein to refer to an enhanced ability of transformants to display a reduction in disease symptoms compared to wild type or control transformants. The disease resistance screen is done with a pathogen that shows susceptible reaction on wild type plants. In one embodiment the pathogen is the fungus *Verticillium dahliae*, as an example of a non host specific resistance. For the screen in *Arabidopsis*, seedlings are grown in the growth chamber at 22-24° C. with 12 hour light, in 10 cm diameter pots containing a mixture of compost:sand:perlite (2:1:1). At two weeks after germination the seedlings are gently uprooted and dipped briefly in a saturated suspension of *Verticillium* culture, and then placed back into the pots with soil covering the roots. The plants are watered normally after a few days pause and examined at various stages for disease symptoms. The plants are scored in 5 pot replicates per genotype and the disease scores taken as the frequency of plants that survive at maturity. The wildtype ecotype Wassilewskija shows no survival in this assay, while disease resistant genotypes show survival ranging from 20-100%.

Transformants expressing high levels of the HRD protein are selected by e.g. analysing copy number (Southern blot analysis), mRNA transcript levels (e.g. RT-PCR using HRD primer pairs or flanking primers) or by analysing the presence and level of HRD protein in various tissues (e.g. SDS-PAGE; ELISA assays, etc). For regulatory reasons, preferably single copy transformants are selected and the sequences flanking the site of insertion of the chimeric gene is analysed, preferably sequenced to characterize the "event". High HRD expressing transgenic events are selected for further crossing/backcrossing/selfing until a high performing elite event with a stable HRD transgene is obtained. Generally, HRD gene expression levels and HRD protein levels will correlate with the drought tolerance phenotype. In one embodiment especially the transgenic seeds derived from such plants are provided, which may be sold as being "drought tolerant".

Transformants expressing one or more HRD genes according to the invention may also comprise other transgenes, such as other genes conferring drought tolerance or conferring tolerance to other biotic or abiotic stresses. To obtain such plants with "stacked" transgenes, other transgenes may either be introgressed into the HRD transformants, or the HRD transformants may be transformed subsequently with one or more other genes, or alternatively several chimeric genes may be used to transform a plant line or variety. For example, several chimeric genes may be present on a single vector, or may be present on different vectors which are co-transformed.

In one embodiment the following genes are combined with one or more HRD genes according to the invention: Genes encoding other Ap2/ERF type transcription factors, preferably ones which have a role in the plant's response to environmental stresses, such as for example the CBF1, CBF2, CBF3 and/or CBF4 encoding genes from *Arabidopsis* (Jaglo-Ottosen et al 1998, Kasuga et al 1999, supra) or orthologs thereof from other species (Dubouzet et al 2003, supra), the SHN genes (Aharoni et al, 2004, supra), with insect resistance genes such as *Bacillus thuringiensis* toxin genes (encoding insecticidal proteins, such as cry genes, vip genes, etc. fungal genes, or other genes.

The stacked transformants may thus have an even broader environmental stress tolerance, to for example salinity, cold stress, insect resistance, pathogen resistance, heat stress, water stress, etc.

It is also possible to introduce or introgress the HRD gene into a plant breeding line which already has a relatively high drought and/or pathogen tolerance, whereby this tolerance may be due to a different underlying molecular mechanism (e.g. root architecture).

B) Non-Transgenic Plants Comprising a Modified Phenotype

It is also an embodiment of the invention to use non-transgenic methods, e.g. mutagenesis systems such as TILLING (Targeting Induced Local Lesions IN Genomics; McCallum et al., 2000, Nat Biotech 18:455, and McCallum et al. 2000, Plant Physiol. 123, 439-442, both incorporated herein by reference) and selection to generate plant lines which produce higher levels of one or more HRD proteins according to the invention. Without limiting the scope of the invention, it is believed that such plants could comprise point/deletion mutations in the promoter that are binding sites for repressor proteins that would make the host HRD gene constitutive or higher in expression. Preferably HRD protein levels in the mutant or parts of the mutant are at least about 2, 5, 10, 15% or more increased in the mutant compared to non-mutant plants. TILLING uses traditional chemical mutagenesis (e.g. EMS mutagenesis) followed by high-throughput screening for mutations (e.g. using Cel 1 cleavage of mutant-wildtype DNA heteroduplexes and detection using a sequencing gel system), see e.g. Henikoff et al. Plant Physiology Preview May 21, 2004. Thus, non-transgenic plants, seeds and tissues comprising an enhanced HRD gene expression in one or more tissues and comprising one or more of the HRD phenotypes according to the invention (e.g. enhanced drought tolerance, enhanced disease resistance, etc., all as described above) and methods for generating and identifying such plants is encompassed herein.

The method comprises in one embodiment the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such mutant plants. Seeds may for example be radiated or chemically treated and the plants screened for a modified HRD phenotype, such as enhanced drought tolerance.

In another embodiment of the invention, the plant materials are natural populations of the species or related species that comprise polymorphisms or variations in DNA sequence at the HRD orthologous coding and/or regulatory sequence. Mutations at the HRD gene target can be screened for using an ECOTILLING approach (Henikoff et al 2004, supra). In this method natural polymorphisms in breeding lines or related species are screened for by the above described. TILLING methodology, in which individual or pools of plants are used for PCR amplification of the HRD target, heteroduplex formation and high-throughput analysis. This can be followed up by selecting of individual plants having the required mutation that can be used subsequently in a breeding program to incorporate the desired HRD-orthologous allele to develop the cultivar with desired trait.

Mutant plants can be distinguished from non-mutants by molecular methods, such as the mutation(s) present in the DNA, HRD protein levels, HRD RNA levels etc, and by the modified phenotypic characteristics.

The non-transgenic mutants may be homozygous or heterozygous for the mutation conferring the enhanced expression of the endogenous HRD gene(s) or for the mutant HRD allele(s).

SEQUENCES

SEQ ID NO 1: *Arabidopsis thaliana* HRD coding sequence

SEQ ID NO 2: *Arabidopsis thaliana* genomic DNA encoding HRD

SEQ ID NO 3: *Arabidopsis thaliana* HRD amino acid sequence

SEQ ID NO 4: Glucocorticoid receptor (GR) domain protein

SEQ ID NO 5: coding sequence of GR domain with flanking sequences for cloning

FIGURE LEGENDS

FIG. 1—The hrd Mutant and 35S::HRD Plants Phenotype.

A Phenotype of young hrd mutant plant showing reduced stature

B) Cross section of leaf of a hrd mutant compared to wild-type, showing more mesophyll cell layers in hrd mutant.

FIG. 2—The root structure of the hrd mutant, compared to wild-type at 3 weeks after germination, showing more profuse secondary and tertiary roots closer to the stem attachment or root base that provides an overall fibrous structure.

FIGS. 3A, 3B and 3C—The hrd mutant, expression analysis and HRD protein structure (SEQ ID NO:3), A) The hrd mutant genomic region showing adjacent tagged genes, annotated as AP2 like and aldolase, with their promoters located 6 kb and 2.3 kb from the CaMV enhancer tetramer of the I-ATag insert.

B) RT-PCR expression analysis of the two genes, AP2-like and aldolase, adjacent the activation tag insert. The RNA used was made from rosette leaves of 2 wild-type samples and the hrd mutant. The aldolase gene expression is unchanged, while the AP2-like gene is overexpressed in the hrd mutant and thus a candidate that confers the phenotype.

C) HARDY amino acid sequence showing the conserved AP2 domain. The shaded box amino acids are identical to the AP2 domain, and the amino-acids in bold are similar to the AP2 domain consensus.

FIG. 4—Induction of HRD-GR by DEX displays the hardy mutant phenotype

The HRD-GR transformed lines were compared to wild-type Ws ecotype and the hid mutant. The genotypes were grown under short day conditions (8 hours daylight) for 4 weeks to increase leaf number. The genotypes were either treated with the steroid inducer DEX or untreated. The DEX treated HRD-GR genotype shows the similar dark green leaf phenotype as the hid mutant.

FIG. 5—Drought Tolerance Experiment with hrd and wild-type.

Fifteen days old seedlings of wild-type Ws, progeny of hrd mutant line, and a positive control rd29-DREB1A line (providing drought tolerance; Kasuga et al. 1999, supra) were exposed for a period of 9 to 12 days of dehydration. Subsequently, seedlings were watered and their appearance after a week (recovery) is presented in the image (apart from the first row at 9 DOD, in which pictures were taken directly at the end of the dehydration period). DOD, Days of dehydration.

FIG. 6—Steroid inducible drought tolerance conferred by a HRD-GR fusion

The 35S::HRD-GR line which showed induction by 10 μM DEX treatment, was tested for drought resistance compared to the hrd mutant and wild-type Ws ecotype. The seedlings of the three genotypes were treated with DEX after germination and compared to untreated genotypes in a drought assay. The day the wild-type death occurred was counted as 1 DAWD (days after wildtype death) and the survival of other genotypes counted in relation to this day. In the first two rows the wildtype is shown displaying dead plants in all samples, and the number of days the other genotypes survived beyond this in each treatment are shown as 1-3 DAWD. The HRD-GR after DEX induction shows clear resistance compared to −DEX treatment, and similar to that as shown by the hrd mutant either + or − DEX treatment.

FIG. 7—Disease resistance of the hrd mutant compared to the wild type.

The hrd mutant (A) compared to a control plant (B), treated with *Verticillium* pathogen (labelled +V) and without *Verticillium* treatment (−V). The hrd mutant is unaffected by *Verticillium*, while the control plant shows a susceptible wilted phenotype.

EXAMPLES

The following non-limiting Examples describe the use of HRD genes for modifying plant phenotypes. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, and Sambrook and Russell (2001) *Molecular Cloning: A Laboratory Manual*, Third Edition, Cold Spring Harbor Laboratory Press, NY; and in Volumes 1 and 2 of Ausubel et al. (1994) Current Protocols in *Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK.

Example 1

Material and Methods 1.1 Plant Material and Drought Tolerance Experiment

All plants, including the activation tag population (Marsch-Martinez et al., 2002, Plant Physiol. 129: 1544-1556) and transgenic lines were grown in the greenhouse at around 22° C. and were in the *Arabidopsis* ecotype Wassilewskija (Ws).

For the drought experiments the activation tagged mutant hardy was compared with the rd29A-DREB-1A line (providing drought tolerance; Kasuga et al., 1999), both in the *Arabidopsis* ecotype Ws. The experiment was conducted in the greenhouse at 22° C., the plants grown in a soil mixture comprised one part of sand and perlite and two parts of compost (a mixture made up of 25% clay and 75% turf with EC ¼ 1 [nitrogen, phosphorous, and potassium]; Hortimea, Elst, The Netherlands). Seeds were sown (after three nights at 4° C.) at density of six plants per 4-cm pot in a tray with 51 pots (Aracon containers; BetaTech, Gent, Belgium). Nutrients (Hydroagri, Rotterdam, The Netherlands; 2.6 EC) were supplied 10 days after germination, and at 2 weeks after germination the plants were subjected to drought (for 9, 10, 11, or 12 days) by transferring the pots to dry trays (after drying each pot from outside). Every 2 days in drought, the plants were moved within the tray to nullify pot position effects. Subsequently, plants were rehydrated and observed for recovery after 1 week. Experiments comparing drought tolerance between the wild type, DREB1A and hrd plants were repeated three times during winter and summer season giving short and long day conditions respectively. In addition drought experiment (with similar growth conditions as described above) with the 35S::HRD-GR fusion containing plants were conducted using DEX induction as described below.

The inducing agent 10 μM DEX was applied in three different ways to the different genotypes (35S::HRD-GR, Ws and hrd) to induce different levels of HRD function: a) DEX applied from the bottom of the pots in a tray, b) sprayed on the top of the plants and c) both from the bottom of pots and sprayed. DEX was applied on the emergence of the first two leaves of the plant and was applied on every alternate day until the 14$^{th}$ day after germination. Then the plants were subjected to drought and rehydrated as described previously and observed for the recovery after 1 week.

1.2 Isolation of Flanking DNA and Sequence Analysis

DNA was isolated according to Pereira and Aarts (1998, Transposon tagging with the En-I system, Totowa, N.J., Humana Press), from two leaves or young flower buds, and 10 ng of genomic DNA was used for Thermal Asymmetric Interlaced-PCR (TAIL PCR) as described by (Marsch-Martinez et al., 2002, supra). A re-PCR was generally performed before sequencing the amplified fragments, and identifying the insert position in the *Arabidopsis* genome using a BlastN algorithm (Altschul et al. 1990, J. Mol. Biol. 215:403-410). Multiple sequence alignments were performed using CLUSTAL X (Thompson et al. 1997, Nucl. Acid Res. 25, 4876-4882) and DNASTAR (DNASTAR Inc. Madison, Wis.) while the GENEDOC (Nicholas et al. 1997, EMBNET News 4, 1-4) and TreeView (Page, 1996, Comp. Applic. Biosci. 12: 357-358) programs were used for editing the alignment and producing the phylogenetic tree, respectively. Phylogenetic analysis including bootstrapping was conducted as described by Lucker et al. (2002, Eur. J. Biochem. 269, 3160-3171).

1.3 Generation of Plant Transformation Constructs and Transgenic *Arabidopsis*

Fragments encoding the genes or regulatory sequences of interest were amplified using pfu DNA polymerase from genomic DNA. In these cases fragments were A-tailed and introduced to the pGEM-T Easy vector as described by the manufacturer (Promega) and subsequently sequenced from both sides before digestion and ligation to the Binary vector. PCR, restriction digests, plasmid DNA isolation and gel electrophoresis were performed using standard protocols.

Fragments encompassing the full length coding regions were amplified (using pfu DNA polymerase) from genomic DNA (for HRD, At2g36450) to generate the overexpression constructs. The genomic DNA used for amplification was from the *Arabidopsis* ecotype Columbia, using primers HRDF and HRDR.

```
Oligonucleotides:
HRDf
                                       SEQ ID NO: 6
(5'-CGGATCCATGCAAGGAACCTCCAAAGAC-3')

HRDr
                                       SEQ ID NO: 7
(5'-CGTCGACGGTTTGTTTAACTATCATGG-3')
```

The pair of oligonucleotides introduced BamHI and SalI restriction sites to the amplified fragments at their 5' and 3', respectively, which were utilized to ligate the 555 bp coding region fragments to the BamHI and SaiI sites in the pNEW1 binary vector (a modified pBI21 binary vector, Nayelli Marsch-Martinez and Andy Pereira, unpublished) in between a 35S promoter of the cauliflower mosaic virus (CaMV) and a nopaline synthase (NOS) terminator. The resulting construct over expressed the At2g36450 AP2 transcription factor under the control of the 35S promoter.

For generating the promoter::GUS constructs, a fragment upstream to the ATG codon of each gene (1 kb of HRD) was amplified from genomic DNA (ecotype Columbia) using Taq DNA polymerase and oligonucleotides which introduced XbaI NcoI restriction sites at the 5' and 3', respectively. This allowed ligation of the fragments to the XbaI and NcoI sites in a modified pBinPlus vector (van Engelen et al., 1995, Trans. Res. 4, 288-290) upstream of the β-glucuronidase (GUS) reporter gene.

For generating the 35S::HRD-GR constructs, a fragment encompassing the full length coding region of HRD was amplified (using pfu DNA polymerase) from young leaf genomic DNA of *Arabidopsis* ecotype Columbia using the oligonucleotides RP6 and RP6 to amplify the 0.55 kb fragment containing the full length coding region of HRD.

```
RP6
                                   SEQ ID NO: 8
5'-TTATTTCTAGAATGCAAGGAACCTCCAAAGAC-3'

RP7
                                   SEQ ID NO: 9
5'-TTATTAGATCTTGGAAAATTCCACAAGTAATCG-3'
```

The pair of oligonucleotides introduced XbaI and BglII restriction sites to the amplified fragments at their 5' and 3', respectively, which were utilized for ligation. The 35S::HRD-GR construct was assembled by multipoint ligations, in which the individual fragments (promoter, HRD gene, GR fragment, terminator) with appropriate compatible cohesive ends were ligated together to the binary vector in one reaction. A CaMV35S promoter fragment extending from −526 to the transcription start site, was obtained as a 0.55 kb HindIII-XbaI fragment from a pBS-SK⁺ derivative of pDH51 (Pietrzak et al., 1986, Nucl Acid Res 14: 5857-68). A GR fragment was obtained as a 0.85 kb BglII-XhoI fragment from pMTL23 (Seq ID 5, coding for GR protein domain Seq ID 4). A CaMV35S terminator fragment was obtained as a 0.21 kb SalI-EcoRI fragment from a pBS-SK⁺ derivative of pDH51 (Pietrzak et al., 1986, supra). The construct was made in the binary vector pMOG22 (ZENECA-MOGEN, NL) which contains a chimaeric CaMV 35S-hygromycin phosphotransferase-tNos for selection during transformation.

The rd29A-DREB1A construct used was similar to that described (Kasuga et al., 1999, Nat. Biotech. 17, 287-291), except that the gene fusion was inserted into pBin-Plus (van Engelen et al., 1995, Trans. Res. 4, 288-290).

The constructs were introduced into the plants using the floral dipping transformation method (Clough and Bent, 1998, Plant J. 16, 735-743). The seeds were plated on one-half-strength Murashige and Skoog medium (½MS; Murashige and Skoog, 1962, Physiol. Plant. 15, 473-497) and seedlings selected on 50 mg/L kanamycin were subsequently transferred to the greenhouse.

1.4 Gene Expression Analyses

Total RNA for Reverse Transcriptase-PCR (RT-PCR) was isolated from mature, green, rosette leaves derived from 4 weeks old hardy activation tag mutant and wild type (ecotype WS) plants using the TrizolReagent as described by the manufacturer (Invitrogen, Life technologies). Approximately 1 μg of total RNA was used for DNase I treatment and cDNA synthesis (using SuperScriptll reverse transcriptase) as described by the supplier (Invitrogen, Carlsbad, Calif.). The cDNA was diluted 50 times and used for amplification using specific oligonucleotides for the actin gene to equalize the concentrations of the cDNA samples.

```
RACTP1,
                                   SEQ ID NO: 10
5'-GCGGTTTTCCCCAGTGTTGTTG-3'

RACTP2,
                                   SEQ ID NO: 11
5'-TGCCTGGACCTGCTTCATCATACT-3'
```

Subsequently the diluted cDNA was utilized to perform a PCR reaction using specific oligonucleotides designed to amplify the two genes flanking the insertion site. Oligonucleotides HRDf and HRDr were used to amplify the At2g36450 gene, and appropriate primers used for the At2g36460 gene. The reaction conditions for PCR included a denaturing step of 95° C. for 3 min, followed by 35 cycles of 1 min at 95° C., 1 min at 55° C., and 1.5 min at 72° C., ending with an elongation step of 5 min at 72° C. For the control PCR with actin oligonucleotides, 30 amplification cycles were used.

1.5 GUS Staining and Microscopy

Tissues from various organs either from soil grown plants or seedlings grown on ½MS in vitro were analyzed for their GUS expression patterns. The GUS solution contained 100 Mm sodium phosphate buffer, pH 7.0, 0.5 mg/ml 5-bromo-4-chloro-3-indolyl β-D glucoronic axid (X-Gluc, Duchefa, The Netherlands), 0.1% Triton, and 0.5 mM each of potassium ferri/ferrocyanide. Samples were vacuum infiltrated and incubated at 37° C. for 16 to 24 h and depleted from chlorophyll in 70% ethanol. Observation were conducted either under the binocular (WILD M3Z of Heerbrugg Switzerland, type-S), or with a light microscope (Zeiss) and an RS Photometrics CoolSNAP camera (MediaCybernetics®) was used to take the digital images, with the corresponding CoolSNAP software.

For Scanning Electron Microscopy (SEM) samples were glued on a sample holder with conductive carbon cement (Leit-C, Neubauer Chemikalien, Germany) and subsequently frozen in liquid nitrogen. The samples were transferred under vacuum to a dedicated cryo-preparation chamber (Ox-ford cryo-system, CT 1500 HF, Eynsham, UK) onto a sample stage at −90° C. Cryo-fractures were made at approx −150° C. using a cold (−196° C.) scalpel blade. The fractured samples were freeze dried for 3 min at −90° C. in vacuum (3×10−7 Pa) to remove water vapour contamination. After the sample surface was sputter-coated with 10 nm Platinum it was transferred to the cold sample stage (−190° C.) inside the Cryo-FESEM (JEOL 6300F Field Emission SEM, Japan, Tokyo) and subsequently analyzed with an accelerating voltage of 5 kV. Images were digitally recorded (Orion, Belgium).

1.6 Microarray Analysis

Total RNA was isolated using TRIZOL reagent (Life Technologies, Inc.) using two-four rosette leaves of *Arabidopsis* according to the manufacturer's instruction and purified using RNeasy Minelute Kit (Qiagen, Carlsbad, Calif., USA). RNA amplification was performed using Amino Allyl MessageAmp Kit (Ambion, Austin, Tex., USA). Briefly, first strand cDNA synthesis was carried out by reverse transcription using 3 μg Total RNA and 1 μl T7 Oligo(dT) primer. Full length dsDNA was synthesized with the reaction containing 1× second strand buffer, 4 μl dNTP mix, 2 μl DNA polymerase, 1 µl RNase H, followed by incubation for 2 h at 16° C. The cDNA was purified by applying to an equilibrated filter cartridge. The purified cDNA was concentrated and the volume adjusted to 14 µl. The antisense RNA amplification by T7 in vitro transcription was achieved in a solution containing 12 µl of ATP, CTP, GTP Mix (25 mM), 3 µl of aaUTP Solution (50 mM), 3 µl of UTP Solution (50 mM), 4 µl of 10× reaction buffer, 4 µl of T7 enzyme mix at 37° C. for 8 h. Then the amplified aRNA was purified by applying to an equilibrated filter cartridge.

For hybridization we used spotted long oligonucleotide Operon array from University of Arizona comprising 29,000 genes of Arabidopsis. The aRNA samples were coupled to mono-reactive NHS esters of Cy3 or Cy5 (Amersham Biosciences) for 2 hrs. After dye quenching and purification, the targets were mixed to 80 µl hybridization solution containing 2×SSC, 0.6× Liquid Blocking Reagent (Amersham Biosciences), and 0.04% SDS. After heating to 95° C. for 2 min and then cooled on ice, the mixture was applied to the gap between the slides and coverslip (LifterSlip, Erie Scientific). Slides were incubated in a hybridization chamber for 9 h at 56° C. in an oven. Slides were washed at RT for 5 min in solutions of 2×SSC with 0.5% SDS, 0.5×SSC, and 0.05×SSC sequentially and then sin dried for 10 min at 1000 rpm.

Hybridized slides were scanned with the ScanArray Express HT scanner (Perkin Elmer), which generates Tiff images of both the Cy3 and Cy5 channels. ScanArray PMT voltage was set from 42 to 50 V depending upon the first sign of a saturated signal. The scanned images were analyzed with the software program ScanArray Express (Perkin Elmer). Adaptive circle method was used for quantification and for data normalization the LOWESS method was used.

Signal to background method was chosen for quality measurement using default parameters (lower limit 400 and multiplier 1.70) and the results used to check efficiency of the experiments.

For further analysis, the data was extracted into Excel spreadsheets and the gene expression values of channel 1 or channel 2 (Cy3 or Cy5) that displayed more than 2× background for the median intensity were selected. In addition we filtered for significant regulated genes that displayed ratios of the medians that were more than 1.5 or less than 0.66 ($Log_2$ values +/−0.58). These gene expression lists provided us with a long list of potential regulated genes that were further used for other comparisons between experimental treatments. In the analysis of specific treatments (e.g. drought) the genes with expressions values of at least one replication more than 2 fold ($Log_2$ values +/−1) were taken to compare to other treatments.

Example 2

Identification of the Hardy Mutant and Characteristic Phenotype

By screening a collection of 2000 Arabidopsis transposon activation tag lines (Marsch-Martinez et al., 2002) a mutant plant was identified with slow growth and dark green leaves. Both rosette and cauline leaves of the mutant (termed hardy, hrd) had thicker leaves when compared to wild type plants. The mutant was later in flowering and had reduced seed set. The most striking phenotype was that it was difficult to pull the mature plant from the soil, presumably due to a strong root structure. The plants seemed very tolerant to changes in the greenhouse conditions thus having the name hardy. Progeny analysis of the self-pollinated hrd mutant line suggested a dominant mutation (three quarters of the plants exhibited the hrd phenotype).

The segregating mutant plants showed difference in their growth pattern and size ranging from medium looking plants to very small plants. The medium sized plants bolted at the same time as wild type indicating that the flowering time was not affected much in these plants, whereas in the smaller plants the bolting started almost 5 to 6 days later compared to the wild type indicating that smaller plants had a later flowering time. However the buds opened much later in the mutant compared to its wild type. In the medium hrd plants the main stem elongated up to 5 to 6 cm tall and had more number of secondary stems of about the same height as the main stem. The internode length was reduced in the stems. The plant looked more bushy and compact. The smaller hrd plants (FIG. 1A) had very short main and secondary stems which did not elongate much due to severe reduction in the internode length. Both medium and short sized hrd plants set lots of flowers compared to wild type but had a low seed set.

The leaf structure was analyzed by making a cryo-fracture SEM of the leaf structure, as described in Example 1.5, revealing much thicker leaf with extra palisade layer compared to wildtype (FIG. 1B). This extra layer probably gives the leaf a deep green phenotype because of the higher density of chlorophyll due to smaller cells and more layers.

The root phenotype was characterized by growing hrd plants in sand with nutrition and washing off the sand to reveal the root structure. The root structure was analyzed by counting and measuring: the number and length of the primary, secondary and tertiary roots (Table 1). The most distinguishing feature of the hrd mutant was a root branching to secondary and tertiary roots (Table 1), very close to the stem or base of the root, just below the soil (FIG. 2). This produced more longitudinal secondary and tertiary roots at the base of the root compared to the wild type giving rise to more complex root structure similar like a fibrous root system of monocot plants. Hence, these roots had more surface area to hold on at the base which increased its anchorage capacity to the soil, making them more resistant to pulling. This phenotype of increased branching close to the root base is a characteristic that contributes to the stronger root phenotype of the hrd mutant. The hrd mutant requires higher root pulling force as determined by applying force pulling the hrd mutant and wild-type plants of about 4-week old. The hrd mutant required between 20-50% more force required to pull out from the ground compared to wild-type. Root pulling force has been shown related to root lodging trait, an important trait in cereals and trees that enables the plants to stand upright and resist lodging (Bruce et al, 2001, J Exp Biol 52: 459-68; Bailey et al 2002, J Exp Biol 53: 333-340).

TABLE 1

| Plant line N = 4 | Measurements of the roots 1 cm from the root base in 3 week old plants | | | |
|---|---|---|---|---|
| | Primary roots (No. of roots ± SD) | Secondary roots (No. of roots ± SD) | Tertiary roots (No. of roots ± SD) | Length of root base (cm) ± SD |
| WT | 1 ± 0.00 | 1.50 ± 0.58 | 0.00 ± 0.00 | 0.55 ± 0.06 |
| hrd | 1 ± 0.00 | 4.25 ± 0.50 | 9.25 ± 1.26 | 0.28 ± 0.05 |

Example 3

An AP2/ERF Transcription Factor Gene is Responsible for the hrd Mutant Phenotype DNA gel blot analysis showed that hrd contains a single insertion (data not shown). Isolation and sequence analysis of DNA flanking the insertion site further indicated that the insertion is located in an intergenic region on chromosome 1 (FIG. 3A). The location of the 35S enhancer tetramer is between a gene encoding an unknown protein (4025 base pairs upstream of the promoter) and a gene encoding a member of the plant specific AP2/ERF family of transcription factors (620 base pairs upstream of the promoter). To examine if these two genes were induced in expression in hrd compared to wild type, we conducted a Reverse Transcription PCR(RT-PCR) experiment using cDNA isolated from hrd and wild type leaf tissues (FIG. 3B).

The results showed that only the AP2/ERF gene AT2g36450 at 6 kb distance from the 35S enhancer tetramer was induced in the hrd mutant leaves compared to wild type leaves and was the prime candidate responsible for the phenotype.

The plant AP2/ERF super-family of transcription factors contains 141 members in *Arabidopsis* (Alonso et al., 2003, Science 301, 653-657), and the HRD protein contains the AP2/ERF domain (FIG. 3C). Sequence homology searches and phylogenetic analysis across the entire AP2/ERF family showed that HRD is similar to a number of proteins in rice (data not shown). The rice and *Arabidopsis* proteins contain the AP2 domain as well as similar amino acid residues in the C-terminal.

Example 4

Transgenic Plants Overexpressing hrd

The downstream gene (At2g36450), encoding the AP2/ERF transcription factor, was the primary candidate responsible for the hrd mutant phenotype. Consequently, the coding region of the gene (termed HRD) was cloned and constitutively expressed in *Arabidopsis* under the control of the 35S CaMV promoter. All the transgenic plants raised (10 individuals) showed a phenotype resembling the original activation tag line, in particular the hrd dark green leaf and smaller structure of the plant (data not shown). The phenotype of most of the 35S::HRD lines (both primary transformants and subsequent generations) was more severe compared to the original hrd mutant. In most cases plants were smaller, and in some cases even dwarfed (3 to 5 cm in size upon maturity) (data not shown).

The same construct was transformed to tobacco and revealed a smaller dark green leaf phenotype showing that the leaf phenotype can be conferred in heterologous plants.

Example 5

Overexpression of the HRD Gene in Rice

A construct was made for rice transformation comprising the HRD coding region under control of the CaMV35S promoter, in the binary vector pMOG22. Transformants were obtained in rice cultivar Nipponbare using established Agrobacterium system. The calli and regenerated shoots were selected for resistance to hygromucin at concentration of 25 mg/l.

After rooting the transformants were transferred to the greenhouse and preliminary phenotypic analysis done. The selfed progeny were then used to do detailed phenotypic and stress tolerance assays. The rice lines transformed with the HRD overexpression construct revealed a root system that was longer with more lateral branches than wild-type. These are features that have been found to be useful to make rice and other cereals more tolerant to drought (Li et al, 2005, TAG 110: 1244-52; Bruce et al 2001 supra).

Example 6

Induction of HRD Expression Using a Glucocorticoid Gene Fusion

To induce the expression of the HRD gene in different tissues and developmental stages, we generated transgenic lines which express a fusion protein of HRD and the hormone binding domain of the rat glucocorticoid receptor (GR; under the control of the CaMV35S promoter) (Chang et al, 1987, Nuc Acids Res, 22: 9603). Seeds of 35S::HRD-GR primary transformants (T1) were sown on plates containing media with or without 10 µM dexamethasone (DEX) hormone. Seedlings sown in media supplemented with DEX showed a clear phenotype as seen in the hrd mutant with shorter seedlings with deep green leaves (FIG. 4).

To characterize the mechanism of HRD expression conferring different phenotypes, experiments to induce the HRD-GR fusion using dexamethosone (DEX) induction at different stages of growth and parts of the plant were carried out. Seedlings and fully grown plants containing the 35S::HRD-GR transgene displayed a wild-type phenotype and no phenotype like the hrd mutants (FIG. 4). Seedlings grown in the greenhouse or growth chamber were treated with DEX at different times after germination (1 week, 10 days after germination) and either from below by irrigation, or sprayed from top or both sprayed and irrigated. The early treatment and treatment by spraying and irrigation generated plants with stronger phenotypes as monitored at the leaf level. The strongest induction was with 10 uM DEX, displaying a phenotype similar to that of the original hrd mutant. The different DEX induced levels of the 35S::HRD-GR transgenic lines were then tested for phenotype of stress induction as outlined below.

The 35S::HRD-GR plants, when treated with 10 µM DEX from below by irrigation, gave a mild hrd phenotype and were bigger than the original hrd mutant. These plants showed slight downward curled, deep green rosette leaves with an elongated stem, having normal looking cauline leaves and normal flowering time (FIG. 4). The size of the rosette leaves was not much affected. The 35S::HRD-GR plants when treated from the top by spraying DEX gave a similar phenotype as hrd with small rosette, slightly curled down with deep green colour. However, the main stem elongated normally up to 7-8 cm tall, and the flowering time ranging from normal to late in some plants. When the 35S::HRD-GR plants were treated both from the bottom (irrigation) and top by spraying DEX they showed a very strong hrd mutant phenotype with very small severely curled deep green rosette leaves and were late in flowering.

Example 7

Spatial and Temporal Expression of the HRD Gene

In order to examine the expression of HRD gene a plant transformation construct was generated, which linked 1.0-kb DNA sequences upstream (as shown in Seq ID 2) of the predicted ATG codon of the gene, to the p-glucuronidase (GUS) reporter gene. In the *Arabidopsis* transformants GUS expression was detected in the seed and embryo. This corresponds with the public microarray data on expression of the HRD gene, suggesting that the gene normally functions during development of the seed, providing stress tolerance during seed maturation.

Example 8

Plants Overexpressing HRD Show Enhanced Drought Tolerance

In order to examine to what extent the change in plant surface, as a result from HRD overexpression, affected its drought tolerance capacity. To do so, 15 day-old seedlings of the original activation tag hrd line, a rd29A-DREB1A resistant control and wild type (ecotype Wassilewskija) were exposed to a period of 9-12 days of dehydration (FIG. 5). Subsequently, seedlings were watered and their recovery monitored for a week. While wild type plants did not recover from the dehydration treatments longer than 9 days and completely dried out, all seedlings derived from lines expressing the HRD gene recovered to become greener and stronger.

The HRD-GR transformants that displayed DEX induction of the hardy associated mutant phenotype of dark green leaves were used for a drought stress experiment. The genotypes WT (wildtype), mutant hrd, and 35S::HRD-GR were germinated and either treated or untreated with DEX. The DEX treatment was provided either from bottom by irrigation, by spraying from to, or both from bottom and sprayed. After 2 weeks of growth, the water was withheld for all treatments and genotypes for a period of 9-15 days. At each day interval, plants were rewatered to be able to test recovery. The day of wild-type (WT) death was noted for each treatment, and the survival of other genotypes and treatments were referred to this date. The Days After Wildtype Death (DAWD) were noted as shown in Table 2. FIG. 6 shows the results of this experiment. The HRD-GR induced with DEX displays a drought tolerance phenotype equivalent to that of the hrd mutant. Comparison of experiments, of DEX treatments from below (irrigation to root), spraying from above (leaf) and both treatments from below and above, showed the combination of treatments gave the most pronounced phenotype for drought tolerance as seen for the leaf phenotype.

TABLE 2

| Plant line | 1 DAWD | 2 DAWD | 3 DAWD |
| --- | --- | --- | --- |
| WT + Dex | 0.00 | 0.00 | 0.00 |
| WT − Dex | 0.00 | 0.00 | 0.00 |
| hrd + Dex | 93.33 | 92.31 | 96.55 |
| hrd − Dex | 93.10 | 96.43 | 83.33 |
| HRD-GR + Dex | 83.33 | 75.00 | 71.43 |
| HRD-GR − Dex | 0.00 | 0.00 | 0.00 |

Similarly, overexpression of HRD in rice also leads to plants with an increased drought tolerance. Transformants with a 35S::HRD construct are able to withstand pro-longed leaf wilting under water deprivation compared to control plants, as assessed by recovery following rehydration.

Example 9

Plants Overexpressing HRD Show Enhanced Disease Tolerance

To test for biotic stress resistance of the HRD overexpression lines a screen for *Verticillium dahliae* resistance was done, as an example of a non host specific resistance. Seedlings were grown in the growth chamber at 22-24° C. with 12 hour light, in 10 cm diameter pots containing a mixture of compost:sand:perlite (2:1:1). At two weeks after germination the seedlings were gently uprooted and dipped briefly in a saturated suspension of Verticilium culture, and then placed back into the pots with soil covering the roots. The plants were watered normally after a few days pause and examined at various stages for disease symptoms. The plants were scored in 5 pot replicates per genotype and the disease scores were taken as the frequency of plants that survived at maturity. The wildtype ecotype Ws showed no survival in this assay, while potential resistant candidate genotypes showed survival ranging from 20-100%.

In replicated infection experiments with *Verticillium*, the hrd mutant displayed high level of resistance displaying none of the wilt symptoms visible in control susceptible wild-type plants (FIG. 7). To confirm the effect of the HRD gene, the resistance tests were repeated in the recapitulated overexpression lines. No wilt symptoms or evidence of pathogen was visible at maturity suggesting a complete resistance phenotype.

Example 10

Microarray Analysis of the hrd Mutant Reveal Genes Responsible for Phenotype

To understand the mechanism of combined abiotic and biotic stress responses, microarray experiments were done with the hrd overexpression mutant. In our studies on screening for drought tolerant *Arabidopsis* genotypes, wild type ecotype Wassilewskija (WS) displayed death after nine days of withholding water, whereas the overexpressor rd29A::DREB1A and hrd lines still survived till 12 days of withholding water. For uniform testing of plant material we used 8 days of water withholding for wild type Ws and harvested leaf sample for RNA isolation, and at the same time took leaf samples from wild type Ws control, rd29A::DREB1A and hrd that were regularly watered. For each comparison (wild type control vs overexpressor) we used two biological replications respectively. The wild type control aRNAs were labeled with Cy3 and the wild type drought or the overexpressor aRNAs were labeled with Cy5 in both biological replications. A number of replications were also done with dye swap experiments as technical control. The experiments were carried out as described in Example 1.6.

In the hrd mutant the microarray experiments reveal 142 induced and 151 repressed genes considering genes consistent in expression in both replications. The Table 3 below shows a selection of the HRD regulon (Set of co-regulated genes) with induced/repressed genes more than two-fold compared to wild-type. The induced genes are shown in red color (or dark shade) and repressed in green color (light shaded).

The pattern of expression of HRD shares partial resemblance to that of DREB1A, suggesting the regulation of genes that confer the stress tolerance phenotype. However a large number of genes are specifically differentially regulated in both HRD and DREB1A overexpressors, as shown for the induced genes in Table 3. The genes specifically induced in the HRD regulon are a set of 4 TFs, $Ca^{2+}$ signaling proteins as well as trehalose and galactinol metabolism genes. The biotic stress related genes are represented by the induced defensin PDF2 genes that have been shown to be induced by pathogen responses in a jasmonate pathway, and repression of the pathogenesis related PR-5 and Bet v1 genes. The difference in HRD and DREB1A in the genes with altered pattern of expression suggests the different mechanism of action or function of these two AP2/ERF genes. These results and comparison to published microarray data indicates that the HRD gene regulates a different set of downstream genes than described before for other AP2/ERF transcription factors. The different set and pattern of regulated genes confer the specific phenotype of the hrd mutant and HRD overexpressor lines.

TABLE 3

Genes upregulated by HRD overexpression compared to DREB1A and Drought

| Name | Annotation | HARDY | | DREB1A | | DROUGHT | |
|---|---|---|---|---|---|---|---|
| | | 129 | 130 | 193 | 195 | 127 | 128 |
| At2g42540 | cold-regulated protein cor15a LEA | 2.62 | 2.24 | 4.31 | 5.83 | 1.4 | 2.09 |
| At5g50720 | ABA-responsive protein (HVA22e) | 2.58 | 2.18 | 4.01 | 6.5 | 1.53 | 2.3 |
| At5g43150 | expressed protein | 2.48 | 1.05 | 1.72 | 1.25 | 2.02 | 1.93 |
| At5g52310 | desiccation-responsive protein 29A (RD29A)/LT178 | 2.32 | 2.1 | 3.48 | 5.48 | 2.42 | 2.87 |
| At5g15970 | stress-responsive protein KIN2/COR6.6 | 2.25 | 2.58 | 1.08 | 3.82 | 2.06 | 2.2 |
| At2g38530 | LTP2: nonspecific lipid transfer protein 2 | 2.14 | 1.97 | 3.82 | 5.47 | 0.94 | 0.87 |
| At3g15210 | ethylene-responsive element-binding factor 4 (ERF4) | 1.81 | 1.56 | 1.38 | 0.72 | 1.26 | 1.52 |
| At1g78070 | WD-40 repeat family protein | 1.78 | 1.12 | 2.95 | 3.46 | 1.06 | 1.19 |
| At1g20440 | dehydrin (Cold-induced COR47 protein) | 1.74 | 1.57 | 4.19 | 5.7 | 1.4 | 1.49 |
| At1g20450 | dehydrin ERD10 (Low-temperature-induced protein LTI45) | 1.56 | 1.47 | 3.52 | 4.17 | 0.99 | 1.39 |
| At5g07010 | similar to steroid sulfotransferase 3 | 4.65 | 4.71 | 2.51 | 2.01 | −0.14 | 0 |
| At4g30650 | low temperature and salt responsive protein LTI6A | 3.91 | 4.34 | 3.11 | 6.7 | −0.29 | 0.27 |
| At3g47540 | chitinase, similar to basic endochitinase CHB4 | 3.59 | 2.75 | 1.69 | 0.65 | 0.15 | 0.63 |
| At4g12470 | protease inhibitor/seed storage/lipid transfer protein (LTP) | 3.44 | 1.29 | 2.71 | 4.56 | 0.06 | −0.67 |
| At2g24560 | GDSL-motif lipase/hydrolase, similar to family II lipase EXL3 | 3.43 | 3.7 | 7 | 7.39 | −0.15 | 0.23 |
| At5g07000 | similar to steroid sulfotransferase 3 | 3.23 | 4.1 | 0.95 | 1.25 | −0.37 | 0.49 |
| At4g12480 | lipid transfer protein (LTP) family protein pEARLI 1 | 3.15 | 1.14 | 5.66 | 5.7 | 1.16 | −1.58 |
| At1g30360 | early-responsive to dehydration stress protein (ERD4) | 2.76 | 2.27 | 2.77 | 3.63 | −0.36 | 0.48 |
| At1g33230 | expressed protein | 2.53 | 2.02 | 3.03 | 4.76 | 0.38 | 0.27 |
| At1g04240 | indoleacetic acid-induced protein 3 (IAA3) | 2.51 | 2.12 | 2.56 | 2.2 | −0.44 | −0.62 |
| At3g16400 | similar to myrosinase-binding protein, Kelch motif | 2.47 | 2.11 | 2.38 | 2.28 | 0.13 | 1.12 |
| At1g54410 | dehydrin family protein | 2.47 | 1.41 | 1.78 | 2.96 | 0.18 | 0.12 |
| At2g02100 | plant defensin-fusion protein (PDF2.2) | 2.34 | 4 | 3.7 | 3.86 | −1.11 | −0.29 |
| At3g09540 | pectate lyase family protein | 2.34 | 2.55 | 1.74 | 1.87 | −0.75 | −0.49 |
| At5g08260 | serine carboxypeptidase S10 family protein | 1.97 | 2.05 | 0.99 | 1.17 | −0.4 | −0.12 |
| At3g53990 | universal stress protein (USP) | 1.94 | 1.31 | 3.66 | 3.72 | −0.02 | −0.08 |
| At3g05880 | hydrophobic protein RCI2A/LTI6A | 1.87 | 1.4 | 2.84 | 4.04 | 0.05 | 0.86 |
| At5g07030 | aspartyl protease family protein | 1.65 | 2.1 | 1.13 | 2.07 | −0.33 | −0.19 |
| At1g08570 | thioredoxin family protein | 1.63 | 1.44 | 4.21 | 4.36 | 0.67 | 0.44 |
| At1g24575 | expressed protein | 1.51 | 1.19 | 1.89 | 1.45 | 0.5 | 0.5 |
| At2g28550 | AP2 domain-containing transcription factor RAP2.7 | 1.3 | 1 | 1.63 | 0.76 | −0.09 | −0.06 |
| At2g26580 | plant-specific transcription factor YABBY family | 1.28 | 1.7 | 1.77 | 2.06 | 0.19 | −0.1 |
| At4g24220 | expressed protein induced upon wounding | 1.2 | 1.2 | 2.03 | 2.25 | 0.57 | 0.45 |
| At5g10860 | CBS domain-containing protein | 1.2 | 1 | 0.88 | 0.8 | 0.25 | −0.04 |
| At1g27030 | expressed protein | 4.86 | 5.09 | 5.79 | 5.53 | −0.63 | −2.36 |
| At2g21660 | glycine-rich RNA-binding protein (GRP7) | 1.17 | 1.82 | 2.79 | 2.53 | −1.82 | −1.86 |
| At4g19120 | early-responsive to dehydration stress protein (ERD3) | 1.16 | 1.37 | 0.75 | 1.03 | −1.82 | −1.01 |
| At5g01600 | ferritin 1 (FER1) | 3.42 | 1.04 | 1.6 | −0.3 | 1.31 | 2.58 |
| At5g22630 | prephenate dehydratase family protein | 2.54 | 3.59 | 0.37 | 0 | 1.9 | 1.56 |
| At2g41180 | sigA-binding protein-related | 1.7 | 1.01 | 1.18 | 0.57 | 0.66 | 0.96 |
| At2g46690 | similar to indole-3-acetic acid induced protein ARG7 | 1.65 | 1.17 | 0.22 | −0.6 | 0.73 | 0.72 |
| At5g41400 | zinc finger (C3HC4-type RING finger) family protein | 1.45 | 1.13 | 1.78 | 0.31 | 1.5 | 1.36 |
| At1g54000 | myrosinase-associated protein, GDSL-like Lipase | 1.17 | 2.56 | 0 | 0 | 1.14 | 0.63 |
| At2g36450 | AP2 domain-containing protein | 5.83 | 5.72 | 0 | −0.3 | 0.19 | −0.5 |
| At2g46970 | basic helix-loop-helix (bHLH) protein | 2.97 | 3.48 | −0.71 | 3.99 | −0.73 | 0.31 |
| At1g78450 | SOUL heme-binding family protein | 2.76 | 2.65 | −0.99 | 1.01 | −0.42 | −0.78 |
| At1g15550 | gibberellin 3 beta-hydroxylase (GA4) | 2.57 | 2.38 | 0 | 0 | −0.37 | −0.33 |
| At1g60140 | trehalose-phosphatase family protein | 2.2 | 1.76 | −0.76 | 1.58 | 0.41 | 0.18 |
| At3g04630 | expressed protein | 2.09 | 1.95 | 1.1 | −0.2 | −0.93 | −0.71 |
| At2g02130 | plant defensin-fusion protein, (PDF2.3) | 1.97 | 2.23 | 0.34 | 2.13 | −0.64 | −0.51 |
| At3g14210 | myrosinase-associated protein | 1.76 | 1.32 | −1.28 | −0.6 | −0.46 | −0.9 |
| At3g06035 | expressed protein (GPI anchored protein) | 1.73 | 1.09 | 0.85 | 0.52 | 0.19 | −0.16 |
| At1g21790 | expressed protein | 1.69 | 1.35 | 3.17 | 0 | 0.28 | 0.8 |
| At5g44130 | fasciclin-like arabinogalactan-protein | 1.69 | 1.33 | −0.06 | 0.25 | −0.61 | −0.72 |
| At2g36460 | fructose-bisphosphate aldolase | 1.66 | 1.56 | 0.79 | 0.51 | 0.06 | 0.03 |
| At4g30660 | Hydrophobic protein RCI2A/LTI6A | 1.59 | 1.16 | −0.37 | 0.89 | −0.26 | −0.4 |
| At4g33490 | nucellin protein | 1.55 | 1.83 | −1.13 | 2.47 | −0.1 | −0.61 |
| At2g27030 | calmodulin-2/3/5 (CAM5) (TCH1) | 1.41 | 1.48 | 2.19 | −0.3 | −0.44 | −0.44 |
| At3g50970 | dehydrin xero2 (XERO2)/LTI30 | 1.39 | 1.14 | 8.89 | 0 | −1.06 | 2.31 |
| At2g03440 | similar to Early nodulin 12B precursor | 1.39 | 1.12 | 0.23 | 0.57 | −0.19 | −0.08 |
| At4g15450 | similar to early-responsive to dehydration stress ERD7 | 1.38 | 1.73 | 0.77 | 0 | 0.77 | 0.39 |
| At5g06710 | homeobox-leucine zipper protein 14 (HAT14)/HD-ZIP 14 | 1.25 | 1.35 | −0.24 | 0.2 | −0.37 | −2.41 |
| At5g50335 | expressed protein | 1.23 | 1.17 | −1.05 | −0.4 | 0.13 | −0.54 |
| At2g21010 | C2 domain-containing protein | 1.21 | 1.47 | 0.37 | 0.53 | 0.01 | 0.15 |
| At3g60530 | zinc finger (GATA type) family protein | 1.19 | 1 | 2.05 | 0 | 0.48 | 0.24 |
| At1g09570 | phytochrome A (PHYA) | 1.12 | 1.48 | −0.32 | 0.6 | 0.04 | −0.7 |
| At1g73480 | hydrolase, similarity to monoglyceride lipase | 1.11 | 1.51 | −1.16 | 2.43 | 0.78 | 0.57 |
| At2g28900 | mitochondrial import inner membrane translocase subunit Tim17 | 2.69 | 2.65 | 0.51 | 5.71 | −1.1 | −0.93 |
| At3g56090 | similar to ferritin subunit cowpea2 precursor | 1.8 | 1.09 | 0.5 | −2.7 | −1.44 | −0.69 |

TABLE 3-continued

Genes upregulated by HRD overexpression compared to DREB1A and Drought

| Name | Annotation | HARDY | | DREB1A | | DROUGHT | |
| --- | --- | --- | --- | --- | --- | --- | --- |
| | | 129 | 130 | 193 | 195 | 127 | 128 |
| At5g11420 | expressed protein | 1.63 | 1.9 | 0.49 | 1.21 | −1.4 | −1.27 |
| At4g32280 | auxin-responsive AUX/IAA family protein | 1.38 | 1.09 | 0 | 0 | −2.57 | −1.52 |
| At2g33370 | 60S ribosomal protein L23 (RPL23B) | 1.3 | 1.14 | 0.26 | 0.68 | −1.19 | −1.54 |
| At3g50740 | UDP-glucoronosyl/UDP-glucosyl transferase family protein | 1.17 | 1.45 | 1.88 | 0 | −1.55 | −1.74 |
| At2g47930 | hydroxyproline-rich glycoprotein | 1.11 | 1.34 | 0.23 | 0.77 | −0.97 | −1.91 |

The invention claimed is:

1. A method for the generation of a transgenic plant having at least one phenotype selected from the group consisting of enhanced disease resistance and enhanced root structure, the method comprising the steps of:
   (a) introducing into cells of plants a chimeric gene comprising a transgenic regulatory sequence active in plant cells operably linked to a nucleic acid sequence encoding a protein comprising SEQ ID NO: 3;
   (b) growing the plant for a period of time and screening the plants for the at least one phenotype to recover a plant containing the chimeric gene as a stable genomic insert, said screening comprising (i) growing the plants in the presence of a pathogen or (ii) examining the root structure of the plants to ascertain the presence of more longitudinal secondary and tertiary roots than in control plants; and, optionally,
   (c) obtaining seed from the recovered plant that contain the chimeric gene as a stable genomic insert and that have the at least one phenotype.

2. The method according to claim 1, wherein said transcription regulatory sequence is selected from the group consisting of: a constitutive promoter, an inducible promoter, a tissue-specific promoter and a developmentally regulated promoter.

3. The method according to claim 1, wherein said transcription regulatory sequence is a stress inducible promoter.

4. The method according to claim 2, wherein said transcription regulatory sequence is a tissue-specific promoter.

5. The method according claim 1, wherein the encoding nucleic acid sequence comprises SEQ ID NO: 1.

6. The method according to claim 1, wherein the screening comprises growing the plants in the presence of a pathogen.

7. The method according to claim 6, wherein the pathogen is a fungus.

8. The method according to claim 7, wherein the fungus is *Verticillium*.

9. The method according to claim 1, wherein the screening comprises examining a root structure of the plants to ascertain the presence of more longitudinal secondary and tertiary roots than in control plants.

10. The method according to claim 1 comprising the step of obtaining seed from the recovered plant that contain the chimeric gene as a stable genomic insert and that have the at least one phenotype.

11. The method according to claim 6 comprising the step of obtaining seed from the recovered plant that contain the chimeric gene as a stable genomic insert and that have the at least one phenotype.

12. The method according to claim 9 comprising the step of obtaining seed from the recovered plant that contain the chimeric gene as a stable genomic insert and that have the at least one phenotype.

* * * * *

SEQUENCE LISTING

<160> NUMBER OF SEQ ID NOS: 11

<210> SEQ ID NO 1
<211> LENGTH: 555
<212> TYPE: DNA
<213> ORGANISM: Arabidopsis thaliana

<400> SEQUENCE: 1

```
atgcaaggaa cctccaaaga caatggcggc cgccacccct tgtacagggg agtaaggcag      60
cgaaagaact caaacaaatg ggtttctgag atccgtgagc cgagaaaacc taaccgtatc     120
tggttaggaa cattctctac ccccgagatg gcggcaatag cctatgacgt ggcagctcta     180
gccctcaaag gcagtcaagc tgagctcaac ttcccaaact cagtttcctc tttgcctgcc     240
ccaacctcca tgtctccagc agacatccaa gcagcagccg cttcggccgc tgctgctttt     300
ggtgctgcta gggatgcgat tgttatggca aataataaca gccaaacaag tggtgtggct     360
tgcatgaata gtagttatga taatacaaat atgaatggat tcatgacgga ggatttggta     420
ttcgacatgc ctaatgtgct catgaatatg gctgaaggaa tgcttcttag ccccctcgt     480
cctactgtct tgatgctgc ttacgacgct gatggttttc ctggaggaga cgattacttg     540
tggaattttc catga                                                     555
```

<210> SEQ ID NO 2
<211> LENGTH: 2000
<212> TYPE: DNA
<213> ORGANISM: Arabidopsis thaliana

<400> SEQUENCE: 2

```
agccaataca ttagttagca tatgaatcta gtacttgttc tgatttattt tctgttaatc      60
aagtttaatt aattagttta caatgtttat gcttgatttt tacatagata tccgacagcc     120
tagtagatca agtgccaacc ggcacgcacc agcagacgta ggtgatagag aaaatttgat     180
ttaattaggt gaatttcttt tttcacacac atacatctat ggtgggaaca aagattccac     240
ggtatatcga gacatgaaat ggatttctta ccctaatcga tttgacaagt ttgaatgaga     300
ataatctaga aaatctatta cattatatta atgtctagtg gggatgataa agcctcaaag     360
aaattgaccc aaacgaaaca gcaatcacac actaacttct tcttagcatt tctaagacac     420
ttttcgatgt gattattcta taaatatccg acccttcacc aagtcaactc tatattcatt     480
tctattctga aataaccatt aaccccaaag taagcaatat ataggaaata catatataca     540
ttatagtctt attatgacat tggagaagtt gtggtttata ccctggaca tggagtgtat     600
atatagcaac attgaaatac agtttcacaa tatgtaaata acacaaaatt ataccaaaaa     660
tattgtaaat cacacaaatg aagtagataa ttttaatttt tattgaagtg ttttcaataa     720
```

| | | |
|---|---|---|
| agtggtgtca agatcatgag aacacatgta ttttcatgaa cctgtgatgg cgaaaacgac | 780 |
| cactttagat agaaacatat atacatcatt tgcaacttaa ttggccacca cccaaaaaaa | 840 |
| cgcgatatcc aacaagagga gcaattaaaa agctgtcttt acagctttag cttcatcatc | 900 |
| tctaagctgt gatcaattcc tcccaaacca ttttctaact ggtttgcact ttcttcactc | 960 |
| tcttctcttc actcttcact acgtacttca ctctccaact aacttaactg caccataaaa | 1020 |
| tggcttcgat ctcttcctct ccttcctcaa actcatcact cttctctact caaaacccta | 1080 |
| atactcatta tcaatatgca aggaacctcc aaagacaatg gcggccgcca cccttgtac | 1140 |
| aggggagtaa ggcagcgaaa gaactcaaac aaatgggttt ctgagatccg tgagccgaga | 1200 |
| aaacctaacc gtatctggtt aggaacattc tctaccccg agatggcggc aatagcctat | 1260 |
| gacgtggcag ctctagccct caaggcagt caagctgagc tcaacttccc aaactcagtt | 1320 |
| tcctctttgc ctgccccaac ctccatgtct ccagcagaca tccaagcagc agccgcttcg | 1380 |
| gccgctgctg cttttggtgc tgctagggat gcgattgtta tggcaaataa taacagccaa | 1440 |
| acaagtggtg tggcttgcat gaatagtagt tatgataata caaatatgaa tggattcatg | 1500 |
| gacgaggatt tggtattcga catgcctaat gtgctcatga atatggctga aggaatgctt | 1560 |
| cttagccccc ctcgtcctac tgtctttgat gctgcttacg acgctgatgg ttttcctgga | 1620 |
| ggagacgatt acttgtggaa ttttccatga tagttaaaca aaccaaccat ataaatatgt | 1680 |
| gattttgtgt gttctatat atgtatgtat gaaataaata aatatggtgt ctagtgatgc | 1740 |
| attgtatgca tggttaggcc cgttaagacc gtaatataag gtcgtactgt attaagtttt | 1800 |
| tgtctttaaa ttattctcaa tttacaatct tatctagtct gatgtaatgc caaatgtaat | 1860 |
| gaatagtcaa tgccttgact gatactcatt tgtttatttt acagatggat acaattttcg | 1920 |
| tagggcttgg tatggttgat atactaatta aatatgtcta atatgattga tatactaatt | 1980 |
| aaatatgtct aatatagaca | 2000 |

<210> SEQ ID NO 3
<211> LENGTH: 184
<212> TYPE: PRT
<213> ORGANISM: Arabidopsis thaliana

<400> SEQUENCE: 3

Met Gln Gly Thr Ser Lys Asp Asn Gly Gly Arg His Pro Leu Tyr Arg
1               5                   10                  15

Gly Val Arg Gln Arg Lys Asn Ser Asn Lys Trp Val Ser Glu Ile Arg
            20                  25                  30

Glu Pro Arg Lys Pro Asn Arg Ile Trp Leu Gly Thr Phe Ser Thr Pro
        35                  40                  45

Glu Met Ala Ala Ile Ala Tyr Asp Val Ala Ala Leu Ala Leu Lys Gly
    50                  55                  60

Ser Gln Ala Glu Leu Asn Phe Pro Asn Ser Val Ser Ser Leu Pro Ala
65                  70                  75                  80

Pro Thr Ser Met Ser Pro Ala Asp Ile Gln Ala Ala Ala Ser Ala
            85                  90                  95

Ala Ala Ala Phe Gly Ala Ala Arg Asp Ala Ile Val Met Ala Asn Asn
            100                 105                 110

Asn Ser Gln Thr Ser Gly Val Ala Cys Met Asn Ser Ser Tyr Asp Asn
        115                 120                 125

Thr Asn Met Asn Gly Phe Met Asp Glu Asp Leu Val Phe Asp Met Pro
    130                 135                 140

```
Asn Val Leu Met Asn Met Ala Glu Gly Met Leu Leu Ser Pro Pro Arg
145                 150                 155                 160

Pro Thr Val Phe Asp Ala Ala Tyr Asp Ala Asp Gly Phe Pro Gly Gly
                165                 170                 175

Asp Asp Tyr Leu Trp Asn Phe Pro
            180

<210> SEQ ID NO 4
<211> LENGTH: 284
<212> TYPE: PRT
<213> ORGANISM: Artificial Sequence
<220> FEATURE:
<223> OTHER INFORMATION: Description of Artificial Sequence:
      Glucocorticoid receptor (GR) domain protein

<400> SEQUENCE: 4

Thr Lys Lys Ile Lys Gly Ile Gln Gln Ala Thr Ala Gly Val Ser
1               5                   10                  15

Gln Asp Thr Ser Glu Asn Pro Asn Lys Thr Ile Val Pro Ala Ala Leu
                20                  25                  30

Pro Gln Leu Thr Pro Thr Leu Val Ser Leu Leu Glu Val Ile Glu Pro
                35                  40                  45

Glu Val Leu Tyr Ala Gly Tyr Asp Ser Ser Val Pro Asp Ser Ala Trp
    50                  55                  60

Arg Ile Met Thr Thr Leu Asn Met Leu Gly Gly Arg Gln Val Ile Ala
65                  70                  75                  80

Ala Val Lys Trp Ala Lys Ala Ile Leu Gly Leu Arg Asn Leu His Leu
                85                  90                  95

Asp Asp Gln Met Thr Leu Leu Gln Tyr Ser Trp Met Phe Leu Met Ala
                100                 105                 110

Phe Ala Leu Gly Trp Arg Ser Tyr Arg Gln Ser Ser Gly Asn Leu Leu
            115                 120                 125

Cys Phe Ala Pro Asp Leu Ile Ile Asn Glu Gln Arg Met Ser Leu Pro
        130                 135                 140

Cys Met Tyr Asp Gln Cys Lys His Met Leu Phe Val Ser Ser Glu Leu
145                 150                 155                 160

Gln Arg Leu Gln Val Ser Tyr Glu Glu Tyr Leu Cys Met Lys Thr Leu
                165                 170                 175

Leu Leu Leu Ser Ser Val Pro Lys Glu Gly Leu Lys Ser Gln Glu Leu
                180                 185                 190

Phe Asp Glu Ile Arg Met Thr Tyr Ile Lys Glu Leu Gly Lys Ala Ile
            195                 200                 205

Val Lys Arg Glu Gly Asn Ser Ser Gln Asn Trp Gln Arg Phe Tyr Gln
    210                 215                 220

Leu Thr Lys Leu Leu Asp Ser Met His Glu Val Val Glu Asn Leu Leu
225                 230                 235                 240

Thr Tyr Cys Phe Gln Thr Phe Leu Asp Lys Thr Met Ser Ile Glu Phe
                245                 250                 255

Pro Glu Met Leu Ala Glu Ile Ile Thr Asn Gln Ile Pro Lys Tyr Ser
                260                 265                 270

Asn Gly Asn Ile Lys Lys Leu Leu Phe His Gln Lys
            275                 280

<210> SEQ ID NO 5
<211> LENGTH: 874
<212> TYPE: DNA
<213> ORGANISM: Artificial Sequence
```

<220> FEATURE:
<223> OTHER INFORMATION: Description of Artificial Sequence: coding
      sequence of GR domain with flanking sequences for cloning

<400> SEQUENCE: 5

```
agatctacaa agaaaaaaat caaagggatt cagcaagcca ctgcaggagt ctcacaagac     60
acttcggaaa atcctaacaa aacaatagtt cctgcagcat taccacagct caccoctacc   120 ttggtgtcac tgctggaggt gattgaaccc gaggtgttgt atgcaggata tgatagctct   180
gttccagatt cagcatggag aattatgacc acactcaaca tgttaggtgg gcgtcaagtg   240
attgcagcag tgaaatgggc aaaggcgata ccaggcttca gaaacttaca cctggatgac   300
caaatgaccc tgctacagta tcatggatg tttctcatgg catttgccct gggttggaga    360
tcatacagac aatcaagtgg aaacctgctc tgctttgctc ctgatctgat tattaatgag   420
cagagaatgt ctctaccctg catgtatgac caatgtaaac acatgctgtt tgtctcctct   480
gaattacaaa gattgcaggt atcctatgaa gagtatctct gtatgaaaac cttactgctt   540
ctctcctcag ttcctaagga aggtctgaag agccaagagt tatttgatga gattcgaatg   600
acttatatca aagagctagg aaaagccatc gtcaaaaggg aagggaactc cagtcagaac   660
tggcaacggt tttaccaact gacaaagctt ctggactcca tgcatgaggt ggttgagaat   720
ctccttacct actgcttcca gacattttg gataagacca tgagtattga attcccagag   780
atgttagctg aaatcatcac taatcagata ccaaaatatt caaatggaaa tatcaaaaag   840
cttctgtttc atcaaaaatg actggatcct cgag                                874
```

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence:
      oligonucleotide HRDf

<400> SEQUENCE: 6

```
cggatccatg caaggaacct ccaaagac                                        28
```

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:
      oligonucleotide HRDr

<400> SEQUENCE: 7

```
cgtcgacggt ttgtttaact atcatgg                                         27
```

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence:
      oligonucleotide RP6

<400> SEQUENCE: 8

```
ttatttctag aatgcaagga acctccaaag ac                                   32
```

<210> SEQ ID NO 9
<211> LENGTH: 33
<212> TYPE: DNA

```
<213> ORGANISM: Artificial Sequence
<220> FEATURE:
<223> OTHER INFORMATION: Description of Artificial Sequence:
      oligonucleotide RP7

<400> SEQUENCE: 9
ttattagatc ttggaaaatt ccacaagtaa tcg                                    33

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:
      oligonucleotide RACTP1

<400> SEQUENCE: 10
gcggttttcc ccagtgttgt tg                                                22

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:
      oligonucleotide RACTP2

<400> SEQUENCE: 11
tgcctggacc tgcttcatca tact                                              24
```